United States Patent
Tei et al.

(10) Patent No.: US 9,452,180 B2
(45) Date of Patent: Sep. 27, 2016

(54) NSAIDS-INDUCED GASTROINTESTINAL MUCOSAL DISORDER ALLEVIATOR AND MANUFACTURING METHOD THEREOF

(71) Applicant: Next21 K.K., Tokyo (JP)

(72) Inventors: Yuichi Tei, Tokyo (JP); Nobuo Sasaki, Tokyo (JP); Shigeki Suzuki, Tokyo (JP)

(73) Assignee: Next21 K.K., Bunkyo-Ku, Tokyo (JP)

( * ) Notice: Subject to any disclaimer, the term of this patent is extended or adjusted under 35 U.S.C. 154(b) by 77 days.

(21) Appl. No.: 14/295,154

(22) Filed: Jun. 3, 2014

(65) Prior Publication Data

US 2014/0323429 A1    Oct. 30, 2014

Related U.S. Application Data

(62) Division of application No. 13/132,613, filed as application No. PCT/JP2009/006603 on Dec. 3, 2009, now abandoned.

(30) Foreign Application Priority Data

Dec. 4, 2008 (JP) ................. 2008-310085

(51) Int. Cl.
| | |
|---|---|
| *C07H 3/04* | (2006.01) |
| *A61K 31/7016* | (2006.01) |
| *A61K 31/192* | (2006.01) |
| *A61K 31/196* | (2006.01) |
| *A61K 31/405* | (2006.01) |
| *A61K 31/5415* | (2006.01) |
| *A61K 31/616* | (2006.01) |
| *A61K 45/06* | (2006.01) |
| *A61K 47/26* | (2006.01) |

(52) U.S. Cl.
CPC ......... *A61K 31/7016* (2013.01); *A61K 31/192* (2013.01); *A61K 31/196* (2013.01); *A61K 31/405* (2013.01); *A61K 31/5415* (2013.01); *A61K 31/616* (2013.01); *A61K 45/06* (2013.01); *A61K 47/26* (2013.01); *C07H 3/04* (2013.01)

(58) Field of Classification Search
None
See application file for complete search history.

(56) References Cited

U.S. PATENT DOCUMENTS

2005/0003000 A1 *  1/2005  Einig ............... A61K 9/145
                                                          424/451

OTHER PUBLICATIONS

Zhang et al., The effects of cryoprotectants on the freeze-drying of ibuprofen-loaded solid lipid microparticles (SLM) European Journal of Pharmaceutics and Biopharmaceutics (2008) vol. 69 pp. 750-759.*

* cited by examiner

*Primary Examiner* — Eric Olson
(74) *Attorney, Agent, or Firm* — Osha • Liang LLP

(57) ABSTRACT

A method of manufacturing a medical drug of alleviating damage of gastrointestinal mucosal induced by a non-steroidal anti-inflammatory drug, NSAID, the medical drug being able to induce anti-inflammatory effect of the NSAID and being able to alleviate damage induced by the NSAID includes dissolving trehalose and the NSAID into one or more solutions, so as to obtain an approximately homogenously-mixed liquid mixture of the trehalose and the NSAID; in which the liquid mixture contains an intermolecular compound with the trehalose and the NSAID; and drying the liquid mixture so as to obtain the medical drug.

5 Claims, 13 Drawing Sheets

NSAIDS-INDUCED GASTROINTESTINAL MUCOSAL DISORDER ALLEVIATOR AND MANUFACTURING METHOD THEREOF

CROSS-REFERENCE TO RELATED APPLICATIONS

This application is a Divisional of U.S. patent application Ser. No. 13/132,613, filed Jun. 3, 2011, which is a national stage application of PCT/JP2009/006603, filed Dec. 3, 2009, which claims priority of Japanese Patent Application No. 2008-310085, filed Dec. 4, 2008. This application claims the priorities and benefits of all these prior applications and incorporates the disclosures of these prior applications by reference in their entireties.

BACKGROUND OF INVENTION

1. Field of the Invention

The present invention relates to medical drugs which reduce damage of gastrointestinal mucosal induced by non-steroidal anti-inflammatory drugs, NSAIDs, and the method for manufacturing thereof.

2. Background Art

NSAIDs, non-steroidal anti-inflammatory drugs, are commonly used as a pain killer, antipyretic, and anti-inflammatory drugs. Even though the NSAIDs have a suitable effect, it has a drawback to induce damage of gastrointestinal mucosal.

Japanese Patent Publication 2005-343886 disclose that damage of gastrointestinal mucosal induced by Ibuprofen, which is categorized in NSAIDs, is reduced by mixing sugars (Patent document 1). However the alleviative effect caused by the mixture of Ibuprofen and sugars at a dry state is not sufficient.

Japanese Patent Publication 2005-139165 disclose that damage of gastrointestinal mucosal induced by NSAIDs including Loxoprofen is reduced by mixing sugars (Patent document 2). However the alleviative effect caused by the mixture of NSAIDs and sugars at a dry state is not sufficient.

Patent document 1: Japanese Patent Publication 2005-343886

Patent document 2: Japanese Patent Publication 2005-139165

SUMMARY OF INVENTION

Problems to be Solved by the Invention

The object of the present invention is to provide medical drugs, which reduce damage of gastrointestinal mucosal induced by NSAIDs.

Means for Solving Problems

The present invention is basically based on the new substance that is intermolecular compounds with NSAIDs and a disaccharide. As shown in the following examples, the intermolecular compounds, new compounds, have extremely high effect to alleviate damage of gastrointestinal mucosal induced by NSAIDs. The present invention is also related to a method for manufacturing the drug medicine which includes a step of manufacturing the intermolecular compounds.

The first aspect of the invention relates to medical drugs which reduce damage of gastrointestinal mucosal induced by non-steroidal anti-inflammatory Drugs, NSAIDs, the medical drugs comprise an intermolecular compound of NSAIDs and a disaccharide; thereby the medical drugs have anti-inflammatory effect of the NSAIDs and can reduce damage induced by the NSAIDs. The medical drugs are manufactured by the method of the invention. The method comprises a step of mixing a disaccharide and the NSAIDs so as to obtain a liquid mixture of the disaccharide and the NSAIDs; and a step of drying the liquid mixture so as to obtain the medical drugs.

As shown in the following examples, the intermolecular compounds, new compounds, have extremely high effect to alleviate damage of gastrointestinal mucosal induced by NSAIDs The examples of medical drugs, which reduce damage of gastrointestinal mucosal induced by NSAIDs, are medical drugs, which reduce damage of gastric mucosal induced by NSAIDs.

As shown in the following examples, the drug medicine of the present invention which is manufactured by the above method interacts with molecular. As shown in the following examples, the drug medicine (lyophilized agent) has reduce damage of gastrointestinal mucosal induced by NSAID better than the mixture of NSAIDs and a disaccharide (mixture of powders). In other words, the drug medicine of the present invention, which is manufactured by the above method, has intermolecular compound between NSAIDs and a disaccharide, thereby the intermolecular compound effectively reduce damage of gastrointestinal mucosal induced by NSAIDs.

As shown in the following working examples preferred NSAIDs are acidic NSAIDs. The example of the NSAIDs is one or more selected from the group of "aspirin, sodium salicylate, salicylamide, sazapirin, diflunisal, ethenzamide, aluminum aspirin, 5-amino salicylic acidic, indomethacin, etodolac, sodium diclofenac, sulindac, sodium anfenac, proglumetacin maleate, acemetacin, nabumeton, mofezolac, ibuprofen, naproxen, loxoprofen, flurbiprofen, flurbiprofen axetil, oxaprozin, tiaprofenic acidic, pranoprofen, aluminoprophen, zaltoprofen, Mefenamic acidic, tolFenamic acidic, alminum flufenamate, ketophenylbutazone, clofezone, bucolome, piroxicam, lornoxicam, tenoxicam, meloxicam, ampiroxicam, epirizole, tiaramide, and elmofazon." Within the above compounds, the preferred NSAIDs are one or more of aspirin, indomethacin, sodium diclofenac, ibuprofen, piroxicam, loxoprofen and Mefenamic acidic. The drug medicine can effectively reduce damage of gastrointestinal mucosal induced by NSAIDs by using the above NSAIDs.

A preferred working example of the first aspect of the invention is that the drug medicine comprises, as the disaccharide, one or more selected from trehalose, maltose, lactose and sucrose. Trehalose is more preferred as the disaccharide.

A preferred working example of the first aspect of the invention is that the form of the medical drugs is tablets, granules, or capsules. The disaccharides and NSAIDs are attached by means of molecular interactions by dissolving disaccharides and NSAIDs jointly, drying the dissolved disaccharides and NSAIDs and forming them into tablets, granules or capsules. Thus such forms of medical drugs bring high reduction effect for damage of gastrointestinal mucosal induced NSAIDs.

A preferred working example of the first aspect of the invention is that the NSAIDs are Indomethacin and the disaccharide is trehalose. Further, the DSC curve of the intermolecular compound obtained by the method of differential scanning calorimetry, DSC, has a first peak and a second peak at 80 to 95° C. and 260 to 270° C., respectively.

A preferred working example of the first aspect of the invention is that the NSAID is ibuprofen and the disaccharide is trehalose. Further the DSC curve of the intermolecular compound obtained by the method of differential scanning calorimetry, DSC, has a third peak and a fourth peak at 175 to 190° C. and 130 to 145° C., respectively.

A preferred working example of the first aspect of the invention is that the NSAID is aspirin and the disaccharide is trehalose. Further the DSC curve of the intermolecular compound obtained by the method of differential scanning calorimetry, DSC, has a first peak and a second peak at 110 to 120° C. and 135 to 145° C., respectively.

A preferred working example of the first aspect of the invention is that the NSAID is sodium diclofenac and the disaccharide is trehalose. Further the DSC curve of the intermolecular compound obtained by the method of differential scanning calorimetry, DSC, has a first peak and a second peak at 90 to 100° C. and 130 to 145° C., respectively.

A preferred working example of the first aspect of the invention is that the NSAID is Mefenamic acidic and the disaccharide is trehalose. Further the DSC curve of the intermolecular compound obtained by the method of differential scanning calorimetry, DSC, has a first peak and a second peak at 225 to 235° C. and 90 to 110° C., respectively. Still further the absolute values of the first peak and the second peak are larger than absolute values of a peak at 225 to 235° C. and a peak at 90 to 110° C. in a DSC curve of Mefenamic acidic obtained by the method of DSC, respectively.

A preferred working example of the first aspect of the invention is that the NSAID is piroxicam and the disaccharide is trehalose. Further the DSC curve of the intermolecular compound obtained by the method of differential scanning calorimetry, DSC, has a first peak and a second peak at 90 to 105° C. and 195 to 205° C., respectively. Still further, the absolute values of the first peak and the second peak are smaller than absolute values of a peak at 90 to 105° C. and a peak at 195 to 205° C. in a DSC curve of Mefenamic acidic obtained by the method of DSC, respectively.

The second aspect of the invention relates to above described medical drugs in which the medical drugs are medical drugs of alleviating damage of gastric mucosal. The medical drugs are manufactured by the method of the invention. The method comprises a step of mixing a disaccharide and the NSAIDs so as to obtain a liquid mixture of the disaccharide and the NSAIDs; and a step of drying the liquid mixture so as to obtain the medical drugs. As shown by the following examples, by making a drug medicine through the above method, it is possible to manufacture a drug medicine which can effectively strengthen the technical effect of the disaccharide that reduce damage of gastrointestinal mucosal induced by NSAIDs.

As shown in the following working examples preferred NSAIDs are acidic NSAIDs. The example of the NSAIDs is one or more selected from the group of "aspirin, sodium salicylate, salicylamide, sazapirin, diflunisal, ethenzamide, aluminum aspirin, 5-amino salicylic acidic, indomethacin, etodolac, sodium diclofenac, sulindac, sodium anfenac, proglumetacin maleate, acemetacin, nabumeton, mofezolac, ibuprofen, naproxen, loxoprofen, flurbiprofen, flurbiprofen axetil, oxaprozin, tiaprofenic acidic, pranoprofen, aluminoprophen, zaltoprofen, Mefenamic acidic, tolFenamic acidic, alminum flufenamate, ketophenylbutazone, clofezone, bucolome, piroxicam, lornoxicam, tenoxicam, meloxicam, ampiroxicam, epirizole, tiaramide, and elmofazon." Within the above compounds, the preferred NSAIDs are one or more of aspirin, indomethacin, sodium diclofenac, ibuprofen, piroxicam, loxoprofen and Mefenamic acidic. The drug medicine can effectively reduce damage of gastrointestinal mucosal induced by NSAIDs by using the above NSAIDs.

Effect of the Invention

The present invention can provide medical drugs, which reduce damage of gastrointestinal mucosal induced by NSAIDs, without decreasing the technical effect caused by NSAIDs.

DETAILED DESCRIPTION

Figure 1:
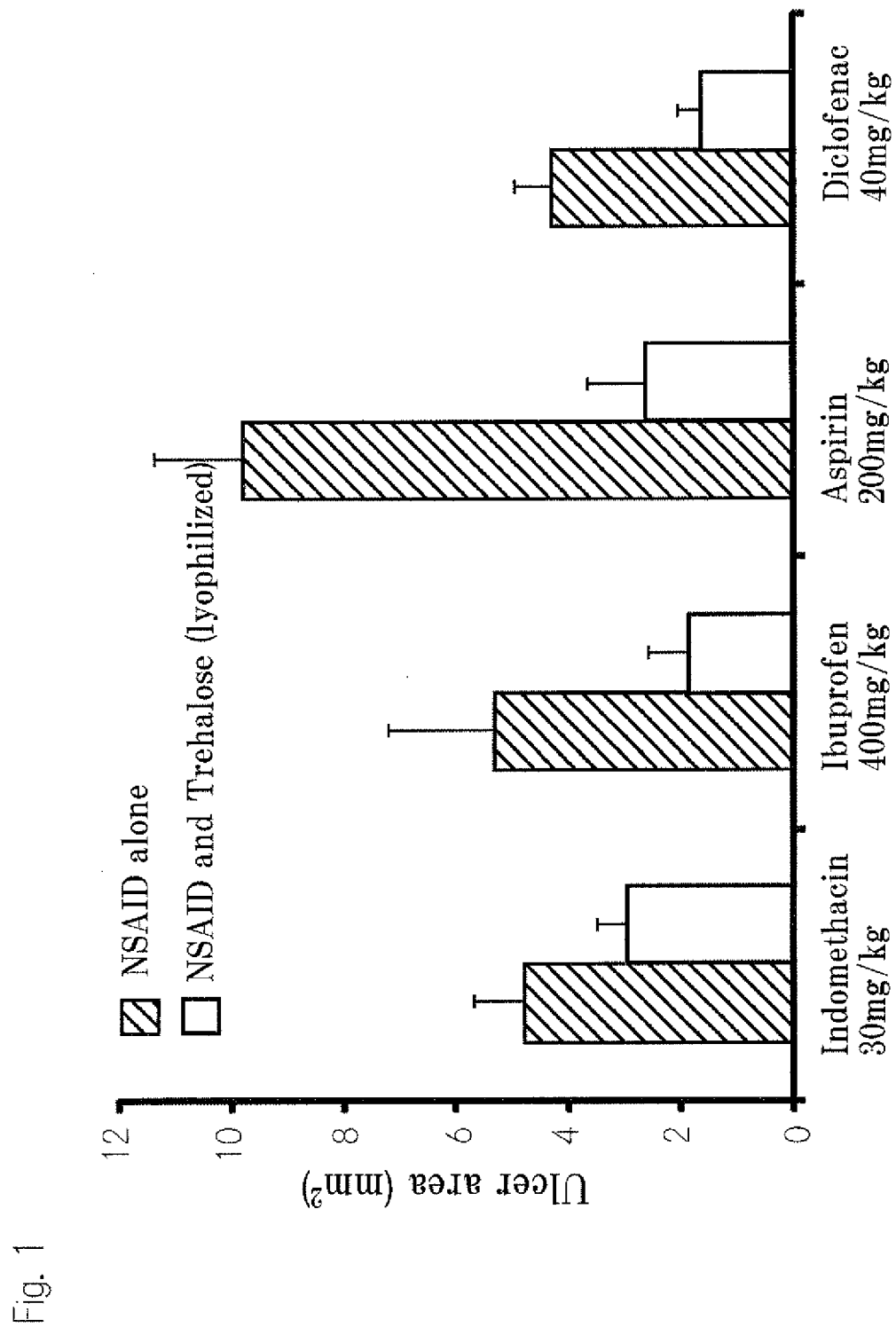
FIG. 1 shows ulcer index ($mm^2$) when test substances are administered.

Best Mode for Carrying Out the Invention

The first aspect of the invention relates to medical drugs, which reduce damage of gastrointestinal mucosal induced by non-steroidal anti-inflammatory drugs, NSAIDs, the medical drugs comprise an intermolecular compound of NSAIDs and a disaccharide; thereby the medical drugs have anti-inflammatory effect of the NSAIDs and can alleviate damage induced by the NSAIDs. The medical drugs are manufactured by the method of the invention. The method comprises a step of mixing a disaccharide and NSAIDs so as to obtain a liquid mixture of the disaccharide and the NSAIDs; and a step of drying the liquid mixture so as to obtain the medical drugs. The liquid mixture comprises dissolved disaccharide and dissolved NSAIDs. Medical drugs, which reduce damage of gastrointestinal mucosal induced by NSAIDs, are drug medicines that can alleviate damage of gastrointestinal mucosal induced by NSAIDs, which keeps the anti-inflammatory effect caused by NSAIDs. It is preferred for the medical drugs of the invention to comprise disaccharide and NSAIDs that have molecular interactions between them. It is preferred for the medical drugs of the invention to comprise an effective amount of disaccharide to alleviate damage of gastrointestinal mucosal induced by NSAIDs. Namely, disaccharide and NSAIDs that have molecular interactions between them are main ingredients for alleviating damage of gastrointestinal mucosal induced by NSAIDs.

In this specification, the term damage of gastrointestinal mucosal induced by NSAIDs includes not only pathological changes of gastric mucosa (e. g. erosion, ulcer, and edema) induced by NSAIDs but also disorders of duodenum which is close part of stomach and disorders of small intestine and large intestine. In this specification, the term Gastrointestinal Tract includes stomach, duodenum, small intestine and large intestine. NSAIDs may bring intestinal perforation at small intestine. The medical drugs, which reduce damage of gastrointestinal mucosal induced by NSAIDs, are effective for an intestinal perforation at small intestine caused by NSAIDs. As shown by the examples, the present invention is most effective for Gastric mucosal disorders. Namely, the most effective working example of the medical drugs, which reduce damage of gastrointestinal mucosal induced by NSAIDs of the present invention, are the medical drugs, which reduce damage of gastric mucosal induced by NSAIDs.

The examples of disaccharide are maltose, sucrose, cellobiose, lactose, and trehalose. Within these disaccharides, the preferred disaccharides are maltose, sucrose, lactose, and trehalose, and most preferable disaccharide is trehalose.

Trehalose is one of disaccharides in which two D-glucoses are connected. Trehalose has three isomers, which are different in their connecting style, α,α body (α-D-glucopyranosyl α-D-glucopyranoside), α,β body (β-D-glucopyranosyl α-D-glucopyranoside)) and β,β body (β-D-glucopyranoyl β-D-glucopyranoside)). As for the present invention, if the medical drugs comprise effective amount of one or more of these isomers in total, it is possible to use any isomers produced by any production method, with any purity and with any states.

NSAIDs, non-steroidal anti-inflammatory drugs, are drug medicines of non-steroidal anti-inflammatory drugs. The drug medicine of the present invention may comprise each of acidic NSAIDs and base NSAIDs. Preferred NSAIDs of the invention are acidic NSAIDs. Further preferred NSAIDs of the invention is Carboxylic acidic NSAIDs. The drug medicine of the invention may comprise one or more kinds of NSAIDs. When the drug medicine comprises 2 or more kinds of NSAIDs, the drug medicine may comprise NSAIDs in the same category (for example, two kinds of salicylic acidic NSAIDs) or NSAIDs in the different categories (for example, salicylic acidic NSAID and Aryl acetic acidic NSAID). These NSAIDs may be manufactured using well known methods or it is possible to use commercially obtainable NSAIDs.

NSAIDs are categorized in salicylic acidic NSAIDs, aryl acetic acidic NSAIDs, propionic acidic NSAIDs, Fenamic acidic NSAIDs, enol acidic NSAIDs, and basic NSAIDs.

The examples of salicylic acidic NSAIDs are aspirin, sodium salicylate, salicylamide, sazapirin, diflunisal, ethenzamide, aluminum aspirin, and 5-amino salicylic acidic.

The examples of aryl acetic acidic NSAIDs are indomethacin, etodolac, sodium diclofenac, sulindac, sodium anfenac, proglumetacin maleate, acemetacin, nabumeton, and mofezolac.

The examples of propionic acidic NSAIDs are ibuprofen, naproxen, loxoprofen, flurbiprofen, flurbiprofen axetil, oxaprozin, tiaprofenic acidic, pranoprofen, aluminoprophen and zaltoprofen.

The examples of Fenamic acid are Mefenamic acidic, tolfenamic acidic, and alminum flufenamate.

The examples of enol acidic NSAIDs are Pyrazolone NSAIDs, Pyrimidine NSAIDs and oxycum NSAIDs. The examples of Pyrazolone NSAIDs are ketophenylbutazone and clofezone. The example of Pyrimidine NSAIDs is bucolome. The examples of oxycum NSAIDs are piroxicam, lomoxicam, tenoxicam, meloxicam, and ampiroxicam.

The examples of basic NSAIDs are epirizole, tiaramide and elmofazon.

It is thought that the drug medicine of the invention has intermolecular bonding by means of molecular interactions. The term intermolecular bonding means that two or more molecules connect each other. The examples of such intermolecular bonding are ionic bonding, complex bonding, hydrophobic bonding, hydrogen bonding, and van der Waals bonding. The drug medicine of the invention, which has such a bonding, can be manufactured by means of the method explained below. It is possible to investigate that the molecular interaction of NSAIDs and disaccharide that are included in the manufactured drug medicine by means of conventional analysis methods. The examples of the analysis methods are DSC (Differential Scanning calorimetry), FTIR (Fourier Transform Infrared Spectroscopy), XPS (X-ray photoelectron spectroscopy) and NMR (nuclear magnetic resonance). The skilled person would be able to analyze the molecular interaction by means of the conventional method.

It is possible for the drug medicine of the invention to comprise a pharmaceutically acceptable carrier or a pharmaceutically acceptable medium. The examples of the pharmaceutically acceptable carrier and a pharmaceutically acceptable medium are the pharmaceutically acceptable substances including an anti oxidant and a retainer. It is possible to use polymers like Polyethylene glycol (PEG), and Conjugated compounds such as cyclodextrin. The followings are the examples but the present invention is not limited to such examples. The examples of the stabilizer are albumin, gelatin, sorbitol, mannitol, lactose, sucrose, maltose, and glucose. The examples of the anti-oxidant are sodium sulfite, ascorbic acidic, tocopherol, cysteine hydrochloride, thioglycolic acidic, and catechol. The examples of the retainer are phenol, thimerosal, and benzalkonium chloride.

The medical drugs of the invention are manufactured by the method of the invention. The method comprises a step of mixing a disaccharide and NSAIDs so as to obtain a liquid mixture of the disaccharide and the NSAIDs; and a step of drying the liquid mixture so as to obtain the medical drugs. The liquid mixture comprises dissolved disaccharide and dissolved NSAIDs. The examples of the step of drying are a step of lyophilize, a step of Granulating and Spray Drying, a step of spray drying and a step of Crushing after drying for granulation. Conventionally, the skilled person would mix powdered NSAIDs and powdered disaccharides to manufacture powdered drug medicine. Further, to manufacture a liquid drug medicine, the skilled person would mix NSAIDs solution and disaccharide solution, would pour powdered NSAIDs and powdered di saccharides separately into a liquid and would stir the solution so as to dissolve the powders, or would pour the mixture of powders that includes powdered NSAIDs and powdered disaccharides into a liquid and would stir the solution so as to dissolve the powders. However, as is shown by the following examples, the mixed solution of NSAIDs solution and disaccharide solution has not sufficient effect to alleviate damage of gastrointestinal mucosal induced by NSAID. The reason of the fact is thought that the disaccharide and NSAIDs in liquid drug medicine do not form intermolecular connections enough. The present invention intentionally makes NSAIDs and disaccharide to be dissolved to obtain a liquid mixture so as to bring interactions and then the present invention makes the liquid mixture to be dried so as to obtain medical drugs that have enough activity to reduce damage of gastrointestinal mucosal induced by NSAID. The drug medicine manufactured by the method has molecular interactions as explained below. Namely, the drug medicine manufactured by the method comprises molecular interactions between disaccharide and NSAIDs. The drug medicine of the invention therefore has NSAIDs molecular dispersed into disaccharide molecules with keeping molecular interactions of NSAIDs and thus it can alleviate damage of gastrointestinal mucosal induced by NSAID effectively.

Step of Mixing

The step of mixing is a step for mixing a disaccharide and NSAIDs so as to obtain a liquid mixture of the disaccharide and the NSAIDs. The liquid mixture comprises dissolved disaccharide and dissolved NSAIDs. The examples of solvates for dissolving disaccharide and NSAIDs jointly are already known solutions that are used for manufacturing drug medicine that includes water, distilled water, de-ionized water, Milli Q water, and saline. It is possible to obtain a liquid mixture by mixing NSAIDs solution and disaccharide solution. It is possible to obtain a liquid mixture by the method that includes dissolving one of powdered NSAIDs and powdered disaccharides to obtain a liquid solution of one ingredient and then dissolving other ingredient into the solution. Further it is possible to obtain a liquid mixture by mixing and dissolving powdered NSAIDs and powdered disaccharides into a liquid. Further it is possible to dissolve NSAIDs into a solvate such as ethanol because NSAIDs has less solubility and make such NSAIDs to be dissolved and then disaccharides are dissolved into the solution to obtain the mixed solution. The example of the weight rate of NSAIDs and disaccharides in the mixed solution is $1 \times 10^2$: $1 \sim 1 \times 10^2$, preferably is $1 \times 10 : 1 \sim 1 : 5 \times 10$ and more preferably is $1 : 1 \sim 1 : 1 \times 30$. The example of the concentration of disaccharide in the mixed solution in manufacturing the medical drugs of the invention is $1 \times 10^{-2} \sim 5 \times 10$ wt %, preferably is $1 \times 10^0 \sim 4.5 \times 10$ wt % and more preferably is $1 \times 10 \sim 4 \times 10$ wt %.

Step of Lyophilization

The step of lyophilization is a step of sublimating water from the freeze sample under decompression circumstance. The step of lyophilization may have following steps.
(1) Cooling the sample (mixed solution) by keeping it for 2 to 3 hours under 4° C., at ordinary pressure (Cooling step);
(2) Freezing the sample by keeping it for 12 to 15 hours under −50° C. at ordinary pressure (Freezing step);
(3) Crystallizing the sample by keeping it for 4 to 6 hours under −20° C. at ordinary pressure (Crystallizing step);
(4) Refreezing the sample by keeping it for 14 to 16 hours under −50° C. at ordinary pressure (Refreezing step);
(5) Drying the sample by keeping it for 24 to 26 hours under −13° C. at 10 to 20 kPa (under high vacuum) (the first drying step);
(6) Drying the sample by keeping it for 10 to 121 hours under 24° C. at 10 to 20 kPa (under high vacuum) (the second drying step); and
(7) Keeping the sample under 24° C. at ordinary pressure.

The method of lyophilization of the above freezes the sample at low temperature and sublimates water (ice) under high vacuum. The lyophilized compound of the invention may be manufactured in accordance with the above described protocol. However, the method of lyophilization is not limited to the above protocol and the skilled person may alter the parameters that include temperatures, pressures, and duration times of each of steps.

Step of Granulating and Spray Drying

The method of Granulating and Spray Drying is a method for obtain dried granules by contacting hot wind to the samples that include moiety with moving the samples. The step of Granulating and Spray Drying is attained by means of already known Granulating and Spray Drying apparatus. The drug medicine of the invention may be manufactured in accordance with the following steps.
(1) Pre-drying the sample by attaching hot wind of 50 to 100° C. with 1 to 2 m/s speed for 10 to 30 minutes to the sample with stirring the sample (mixed solution) (pre drying step);
(2) Granulating the sample by attaching hot wind of 20 to 50° C. with 2 to 3 m/s speed for 30 minutes to 1 hour to the sample (granulating step);
(3) Drying the sample by attaching hot wind of 50 to 100° C. with 1 to 2 m/s speed for 30 minutes to 2 hours to the sample (drying step); and
(4) Cooling the sample by attaching cool wind of 5 to 20° C. with 1 to 2 m/s speed for 10 minutes to 60 minutes to the sample (cooling step).

The method of Granulating and Spray Drying obtain granules by attaching hot wind to the sample so as to dry the sample with the sample floating in the air. The drug medicine of the invention may be manufactured in accordance with the above described protocol. However, the method of Granulating and Spray Drying is not limited to the above protocol and the skilled person may alter the parameters that include temperatures, pressures, and duration times of each of steps.

The examples of the form of the medical drugs of the invention when the medical drugs are manufactured by means of the method of Granulating and Spray Drying are tablets, granules, or capsules. It is possible to manufacture tablets, granules, or capsules by compacting medical drugs using conventional compacting method, in which the medical drugs are manufactured by wet granulating method. It is possible to obtain capsule drug medicine by filling tablets or granules into the capsule. The volume of the each of the drug medicine is not limited but it is possible to adjust the volume based on the amount of disaccharides and NSAIDs. The disaccharides and NSAIDs are attached by means of molecular interactions by dissolving disaccharides and NSAIDs jointly, drying the dissolved disaccharides and NSAIDs and forming them into tablets, granules or capsules.

Such forms of medical drugs bring high alleviative effect for damage of gastrointestinal mucosal induced by NSAIDs. Thus, the above described forms of the medical drugs are preferred.

Step of Spray Drying

The step of spray drying (Step of spray drying) is a step of drying object quickly by spraying liquid samples with heated wind though narrow nozzle such that the samples become minute drops in the chamber. It is possible to manufacture the spray dried object by means of a conventional spray dryer. It is possible to manufacture the medical drugs of the invention using the following steps.
(1) Spraying samples (mixed solution) though nozzle with 0.5 to 1 mm aperture with heated wind of 100 to 300° C. into the chamber, with air pressure of 0.5 to 2.5 kg/m$^2$ and flow speed of 25 to 50 l/min (spray step);
(2) Drying sprayed samples by contacting heated wind of 100 to 300° C. with flow speed of 0.5 to 1 m/s for 30 seconds to 5 minutes (drying step).

As described the above the method of spray drying is the method for drying and granulating samples by contacting heated wind to the minute drops that are made by spraying the sample into high temperature chamber. It is possible to manufacture the medical drugs of the invention by means of the above method. However, the invention is not limited to the medical drugs manufactured by the above method. It is possible for the skilled person to adjust the parameters that include temperature and duration time for each step.

Step of Crushing after Drying for Granulation

The step of crushing after drying for granulation is a step for manufacturing granules by crushing dried samples that contained moiety. It is possible to manufacture the medical drugs of the invention based on the following steps.
(1) Stirring samples (mixed solution) for 1 to 5 hours with attaching hot wind of 50 to 80° C. and stirring speed of 10 to 100 round per minute (drying step);
(2) Cooling samples by contacting cold wind of 5 to 15° C. with the dried samples (Cooling step);
(3) Crushing the cooled samples by means of a crasher (crushing step); and
(4) Sieving the crashed samples by means of a sieving apparatus with predetermined size of sieves (sieving step).

As described the above the method of Crushing after drying for granulation is a method for manufacturing a powders with predetermined size by crashing lump of samples. It is possible to manufacture the medical drugs of the invention by means of the above method. However the invention is not limited to the medical drugs manufactured by the above method. It is possible for the skilled person to adjust the parameters that include temperature and duration time for each step.

It is possible to manufacture the molecular compound of disaccharide and NSAIDs by melting and mixing disaccharide and NSAIDs under an anaerobic condition and at the temperature higher than the melting point of disaccharide and NSAIDs. However, the medical drugs manufactured by the above methods were superior to the medical drugs manufactured by the method in the effect of alleviating damage of gastrointestinal mucosal induced by NSAID effectively.

The apparatus for dissolving and mixing is already known. It is possible to use such conventional apparatus to execute the dissolving and mixing step. The example of apparatus for executing the dissolving and mixing step is a satirizing apparatus. It is possible to obtain crystal of molecular compound by stirring mixed solution of disaccharide and NSAIDs at the temperature that is higher than the melting point of disaccharide and NSAIDs and by executing static crystallization after the stirring for predetermined time. It is possible to obtain molecular compound with high purity by repeating the processes of melting, stirring and executing static crystallization.

The melting and mixing step is executed under an anaerobic condition. More specifically, the melting and mixing step is executed under the existence of nitrogen gas or inert gas. The examples of the inert gas are noble gases and the examples of the novel gases are helium, neon, argon, and krypton. Within the noble gasses, argon is most preferred.

The melting and mixing step is executed under atmospheric pressure, reduced pressure and high pressure. It is possible to use conventional catalyst at the melting and mixing step.

It is possible to obtain the molecular compound of disaccharide and NSAIDs by contact melting of crystals of disaccharide and NSAIDs as well as the method as described above. However, the medical drugs manufactured by the above methods were superior to the medical drugs manufactured by the method in the effect of alleviating damage of gastrointestinal mucosal induced by NSAID effectively.

It is possible to execute the contact melting of disaccharide and NSAIDs by means of a bicrystal furnace. The bicrystal furnace is an apparatus that can control the boundary at which seed crystals contact (grain boundary) and grow the seed crystals by melting contacted part of ingredients crystals and moving the cast. More specifically, the method of contact melting is the method that comprises crashing crystals of disaccharide and NSAIDs continuously for a long period, locally dissolving contacted points of crystals and growing the molecular compound of disaccharide and NSAIDs.

The medical drugs of the invention manufactured as described the above has effects of anti-inflammatory, analgesic, and antipyretic of NSAIDs. The medical drugs of the invention, which comprises disaccharide and NSAIDs, can alleviate damage of gastrointestinal mucosal induced by NSAID and thus it is possible to be used for the patients whom NSAIDs are effective to cure or prevent diseases to take an effective amount of the medical drugs of the invention. In other words, the present invention provides a method for treatment or prevent method which include a step of giving medical drugs, which reduce damage of gastrointestinal mucosal induced by NSAIDs, to an object. The object may be a human. The preferred examples of the medical drugs, which reduce damage of gastrointestinal mucosal induced by NSAIDs that comprises disaccharide and NSAIDs with molecular interactions, are the medical drugs, which are manufactured by a step of lyophilization or a step of wet granulating.

NSAIDs usually have stimulated taste such as sour taste and bitter taste and thus the taste of NSAIDs is not suitable for oral doses. However, the medical drugs of the invention comprise disaccharide as well as NSAIDs, in which disaccharide and NSAIDs have molecular interactions. The disaccharide softens the taste of NSAIDs. Thus, it is possible to improve the taste of tablets that comprise NSAIDs and, especially the taste of granules. The medical drugs of tablet form, especially of granules, are easy to take. Further, anti-oxidant effect of disaccharide strengthens the chemical stability of NSAIDs.

The medical drugs manufactured by the above method is mainly used for oral doses. However, it is possible to use the medical drugs of the invention to non oral doses. When the medical drugs of the invention is used as an oral dose, the patient shall take the medical drugs together with a pharmaceutically acceptable solution such as water. The example of non oral dose is syringe. When the medical drugs of the invention is given by means of syringe, the medical drugs should be dissolved into a predetermined pharmaceutically acceptable solvent such that the solution contains predetermined concentrate. The examples of the pharmaceutically acceptable solvent are water for injection, saline solution, and glucose solution.

The amount of dose varies in accordance with the kind of patient, the age of patient and symptoms. In general, the daily dose is from 10 mg to 1000 mg, preferably from 100 mg to 500 mg, of NSAIDs as a part of an active ingredient. It is possible to give the medical drugs of the invention twice to five times a day. By giving the medical drugs separately to several times it is possible to escape drastic change of concentrate of the medical drugs in blood and it is possible to prevent side effect and reduce load to the patient.

A preferred working example of the invention is to provide a use of disaccharide and NSAIDs in manufacturing medical drugs, which reduce damage of gastrointestinal mucosal induced by NSAIDs. Further the present invention provide a use of disaccharide and NSAIDs that have intermolecular bonding for manufacturing medical drugs, which reduce damage of gastrointestinal mucosal induced by NSAID. A preferred example of the disaccharide and NSAIDs that have intermolecular bonding are those manufactured by the methods of lyophilization or wet granules. It is possible to use the above explained one or more kinds of NSAIDs.

We explain the working examples of the invention. However the invention is not limited to the following examples.

Working Example 1

The reduce effect of trehalose for the damage of gastrointestinal mucosal induced by NSAIDs 1. Test Samples In this example, aspirin, indomethacin, ibuprofen, and sodium diclofenac were used as NSAIDs. We bought aspirin, indomethacin and ibuprofen from Wako Pure Chemical Industries and bought sodium diclofenac from Cayman Inc. We used trehalose manufactured by Hayashibara and used Sodium carboxy-methyl cellulose manufactured by Dai-ichi Kogyo Seiyaku Co., Ltd.

2. Preparation of Lyophilized Trehalose•NSAIDs

We prepared 30% (w/v) trehalose solution using purified water (Milli Q grade (milli Q water)). Suitable amount of NSAIDs were dissolved in 99.5% ethyl alcohol and mixed with trehalose solution at suitable ratio. After enough stirred, the mixed solutions were dried for more than 48 hours by means of a lyophilizing apparatus (Tokyo Rika Co., EYELA, lyophilizing apparatus, FDU-1100).

Specifically the preparation was executed by the following steps.
(1) Trehalose was dissolved in milli Q water so as to obtain 30% (w/v) trehalose solution
(2) 1.0 g of each of NSAIDs was dissolved in 2.0 mL ethyl alcohol.
(3) Suitable amount of trehalose solutions were added to the ethyl alcohol solutions, in which each of NSAIDs was dissolved. Please note that indomethacin and ibuprofen solution brings precipitation if all of the trehalose solution required were to be added. Thus as for the indomethacin and ibuprofen solution, maximum amount of trehalose solutions which were not bring precipitation were added and then the mixed solutions were stirred for about 10 to 20 minutes.
(4) Milli Q water was added so that the final concentrate of ethyl alcohol to be less than 10%, preferably less than 5%. As for aspirin and sodium diclofenac, it was not found precipitated. Thus each of the solutions of and sodium diclofenac was stirred for about 10 to 20 minutes.
(5) The mixed solutions were dried for more than 48 hours by means of a lyophilizing apparatus (Tokyo Rika Co., EYELA, lyophilizing apparatus, FDU-1100).

Each of the test substances were adjusted by suspending or dissolving them into 0.5% CMC.Na solution. Each of 9 mL of Liquid doses was given per 1 kg weight by oral dose. 0.5% CMC.Na solutions were given to control group.

3. Animal

We bought Winster male rats (Japan SLC) that were 8 weeks old. We breed these rats keeping 20 to 26° C., humidity of 30 to 70%, housing 2 to 3 rats in a rat breeding gage (mouse and rat breeding CE-2), giving enough amount of filtered tap water. After breeding 7 days, 5 to 10 rats per group were picked to execute the example. The rats were fasting for 24 hours without giving any food and then the rats were fed no food and no water for 1 hour just before the examination.

4. Method

From 11 AM on the previous day of the examination date, the rats were kept fasting and test substances were fed though mouse. After 5 hours passed, these rats were killed by carbon dioxide gas and stomachs were picked up. The duodenums were tagged. 6 mL of neutral formalin was poured from the esophagus so as to fix the stomachs for 30 minutes. The stomachs were cut along with the greater curvature. The cut stomachs were gently washed by saline, the presence of blood spot were observed by a stereoscopic microscope. The area of blood spots was measured by 0.5 mm×0.5 mm unit as an index of ulcer and the sum of each animal was calculated. The rate of suppressed ulcer was calculated, using the ulcer index for the group in which each of test sample was given and the group in which trehalose was also given, in accordance with the following equation.

Rate of suppressed ulcer (%)=$[1-A/B]\times100$

A: Ulcer index for the group in which NSAID was given alone
B: Ulcer index for the group in which NSAID and trehalose was given 5. Result Obtained rate of suppressed ulcer for the group in which trehalose was also given was shown in Table 1 and FIG. 1.

TABLE 1

| Test substances (mg/kg) | Rate of suppressed ulcer (%) |
| --- | --- |
| Indomethacin (30) + Trehalose (800) | 38.3 |
| Ibuprofen (400) + Trehalose (800) | 64.5 |

TABLE 1-continued

| Test substances (mg/kg) | Rate of suppressed ulcer (%) |
|---|---|
| Aspirin (200) + Trehalose (800) | 71.6 |
| Diclofenac (40) + Trehalose (800) | 61.6 |

FIG. 1 shows ulcer index ($mm^2$) when test substances are administered. The horizontal axis of FIG. 1 indicates that the tested substances that were administered. The vertical axis of FIG. 1 indicates the area of ulcer. The result shows that, for all of NSAIDs, when lyophilized NSAIDs as well as trehalose were administered have a tendency to suppress the generation of ulcer compared to NSAIDs alone were administered.

The stomach ulcer model induced by indomethacin was examined. When indomethacin alone (30 mg/kg) was administered ulcer of 4.83±0.90 (average of 10 cases±standard deviation) $mm^2$ was observed. When lyophilized indomethacin and trehalose (30 mg/kg of indomethacin and 800 mg/kg of trehalose) was administered 2.98±0.90 (average of 10 cases±standard deviation) $mm^2$ was observed. Thus the rate of suppressed ulcer caused by lyophilizing was 38.8%.

The stomach ulcer model induced by ibuprofen was examined. When ibuprofen alone (400 mg/kg) was administered ulcer of 5.35±1.86 (average of 5 cases±standard deviation) $mm^2$ was observed. When lyophilized ibuprofen and trehalose (400 mg/kg of ibuprofen and 800 mg/kg of trehalose) was administered 1.90±0.69 (average of 5 cases±standard deviation) $mm^2$ was observed. Thus the rate of suppressed ulcer caused by lyophilizing was 64.5%.

The stomach ulcer model induced by aspirin was examined. When aspirin alone (200 mg/kg) was administered ulcer of 10.40±2.80 (average of 5 cases±standard deviation) $mm^2$ was observed. When lyophilized aspirin and trehalose (200 mg/kg of aspirin and 800 mg/kg of trehalose) was administered 3.00±1.20 (average of 5 cases±standard deviation) $mm^2$ was observed. Thus the rate of suppressed ulcer caused by lyophilizing was 71.2%.

The stomach ulcer model induced by diclofenac was examined. When diclofenac alone (40 mg/kg) was administered ulcer of 4.30±0.71 (average of 10 cases±standard deviation) $mm^2$ was observed. When lyophilized diclofenac and trehalose (40 mg/kg of diclofenac and 800 mg/kg of trehalose) was administered 1.65±0.43 (average of 10 cases±standard deviation) $mm^2$ was observed. Thus the rate of suppressed ulcer caused by lyophilizing was 61.6%.

The working example 1 shows that by using lyophilized NSAIDs and trehalose, it is possible to suppress ulcer.

Working Example 2

Suppression of Gastric mucosal disorder by molecular interactions between trehalose and NSAIDs 1

1. Test substances

In this example, indomethacin, aspirin and sodium diclofenac were used as NSAIDs. We bought indomethacin from Wako Pure Chemical Industries and bought sodium diclofenac from Cayman Inc. We used trehalose manufactured by Hayashibara and used. Sodium carboxy methyl cellulose manufactured by Dai-ichi Kogyo Seiyaku Co., Ltd.

2. Preparation of Lyophilized Trehalose•NSAIDs

We prepared 30% (w/v) trehalose solution using purified water (Milli Q grade (milli Q water)). Suitable amount of NSAIDs were dissolved in 99.5% ethyl alcohol and mixed with trehalose solution at suitable ratio. After enough stirred, the mixed solutions were dried for more than 48 hours by means of a lyophilizing apparatus (Tokyo Rika Co., EYELA, lyophilizing apparatus, FDU-1100).

3. Preparation of Liquid Dose

The liquid doses were prepared on the date when the examination was executed. Weighted NSAIDs were suspended or dissolved into 0.5% CMC.Na solution to prepare dozes of administrating NSAIDs only. Suspension of NSAIDs and solution of trehalose were prepared. Then the same amount of the suspension and solution were mixed to prepare the dozed of mixture of trehalose and NSAIDs just before administrating them. Predetermined amount of lyophilized compounds that contains lyophilized trehalose and NSAIDs with predetermined rate were weighted and each of them was mixed with 0.5% CMC.Na solution to prepare dozes of lyophilized trehalose and NSAIDs. For each groups the amount of dose was 8 mL per kg or rat.

4. Animal

We bought Winster male rats (Japan SLC) that were 8 weeks old. We breed these rats keeping 20 to 26° C., humidity of 30 to 70%, housing 2 to 3 rats in a rat breeding gage (mouse and rat breeding CE-2), giving enough amount of filtered tap water. After breeding 7 days, 5 to 10 rats per group were picked to execute the example. The rats were fasting for 24 hours without giving any food and then the rats were fed no food and no water for 1 hour just before the examination.

5. Method of Producing Gastric Mucosal Disorder and Evaluation

From 11 AM on the previous day of the examination date, the rats were kept fasting and test substances were fed though mouse. After 5 hours passed, these rats were killed by carbon dioxide gas and stomachs were picked up. The duodenums were tagged. 6 mL of neutral formalin were poured from the esophagus so as to fix the stomachs for 30 minutes. The stomachs were cut along with the greater curvature. The cut stomachs were gently washed by saline, the presence of blood spot were observed by a stereoscopic microscope.

The area of blood spots was measured by 0.5 mm×0.5 mm unit as an index of ulcer and the sum of each animals was calculated. The rate of suppressed ulcer was calculated, using the ulcer index for the group in which each of test samples were given and the group in which trehalose was also given, in accordance with the following equation.

Rate of suppressed ulcer (%)=$[1-A/B] \times 100$

A: Ulcer index for the group in which NSAID was given alone

B: Ulcer index for the group in which NSAID and trehalose was given

6. Result

Measured area of ulcer for the groups in which indomethacin alone was given, mixed indomethacin and trehalose, and lyophilized indomethacin and trehalose were given was shown in Table 2.

TABLE 2

| Test substances (mg/kg) | Ulcer index (mm², average ± standard deviation) |
|---|---|
| Indomethacin alone | 4.83 ± 0.90 |
| Indomethacin + Trehalose (mixed) | 4.15 ± 0.86 |
| Indomethacin + Trehalose (lyophilized) | 2.98 ± 0.54 |

Measured area of ulcer for the groups in which aspirin alone was given, mixed aspirin and trehalose, and lyophilized aspirin and trehalose were given was shown in Table 3.

TABLE 3

| Test substances (mg/kg) | Ulcer index (mm², average ± standard deviation) |
|---|---|
| Aspirin alone | 10.40 ± 2.73 |
| Aspirin + Trehalose (mixed) | 9.25 ± 3.45 |
| Aspirin + Trehalose (lyophilized) | 2.95 ± 1.14 |

Measured area of ulcer for the groups in which diclofenac alone was given, mixed diclofenac and trehalose, and lyophilized diclofenac and trehalose were given was shown in Table 4.

TABLE 4

| Test substances (mg/kg) | Ulcer index (mm², average ± standard deviation) |
|---|---|
| Diclofenac alone | 4.30 ± 0.71 |
| Diclofenac + Trehalose (mixed) | 4.20 ± 1.11 |
| Diclofenac + Trehalose (lyophilized) | 1.65 ± 0.43 |

Figure 2:
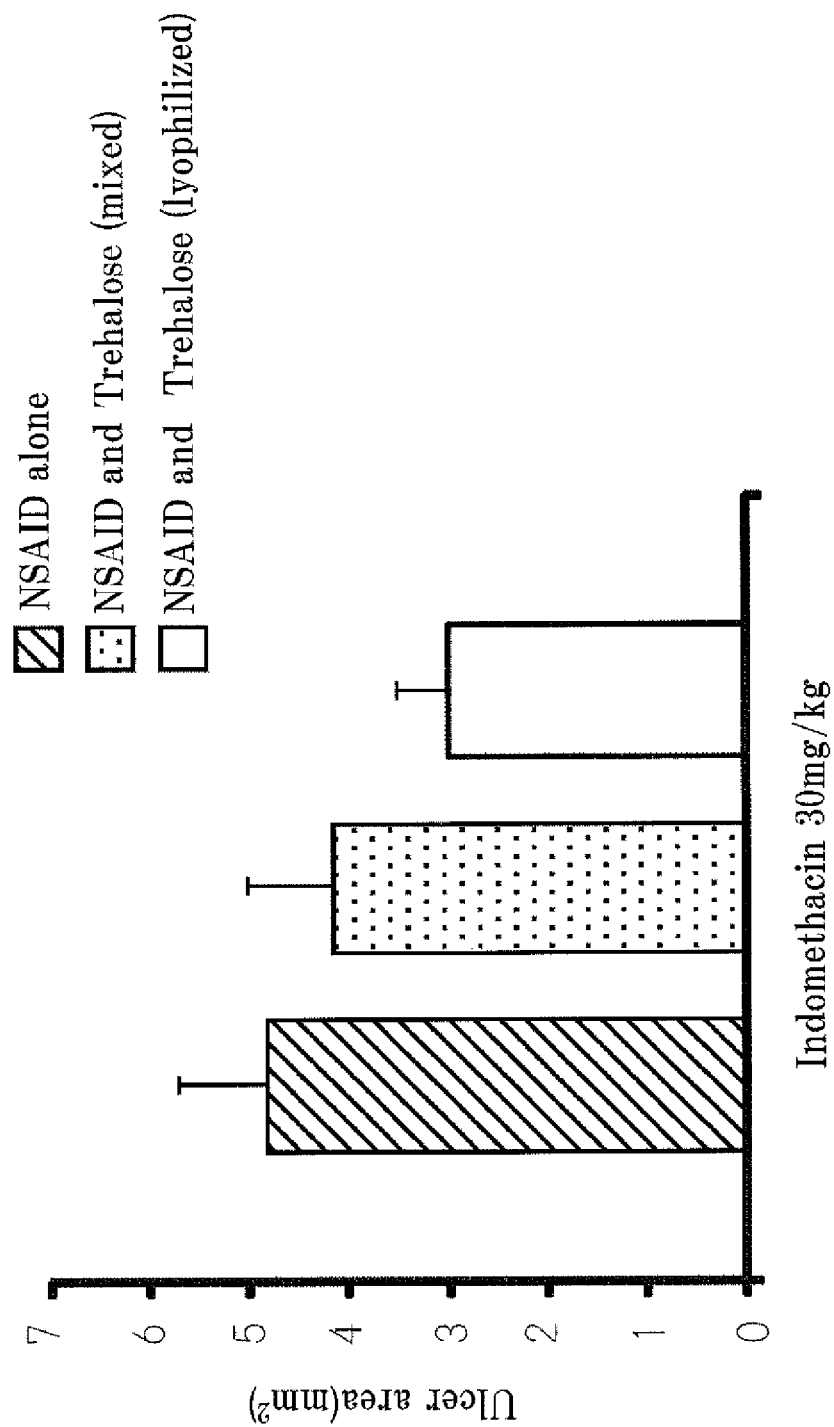
FIG. 2 shows a rat ulcer index ($mm^2$) when indomethacin alone, a mixture of indomethacin and trehalose and lyophilized indomethacin and trehalose are administered.
Figure 3:
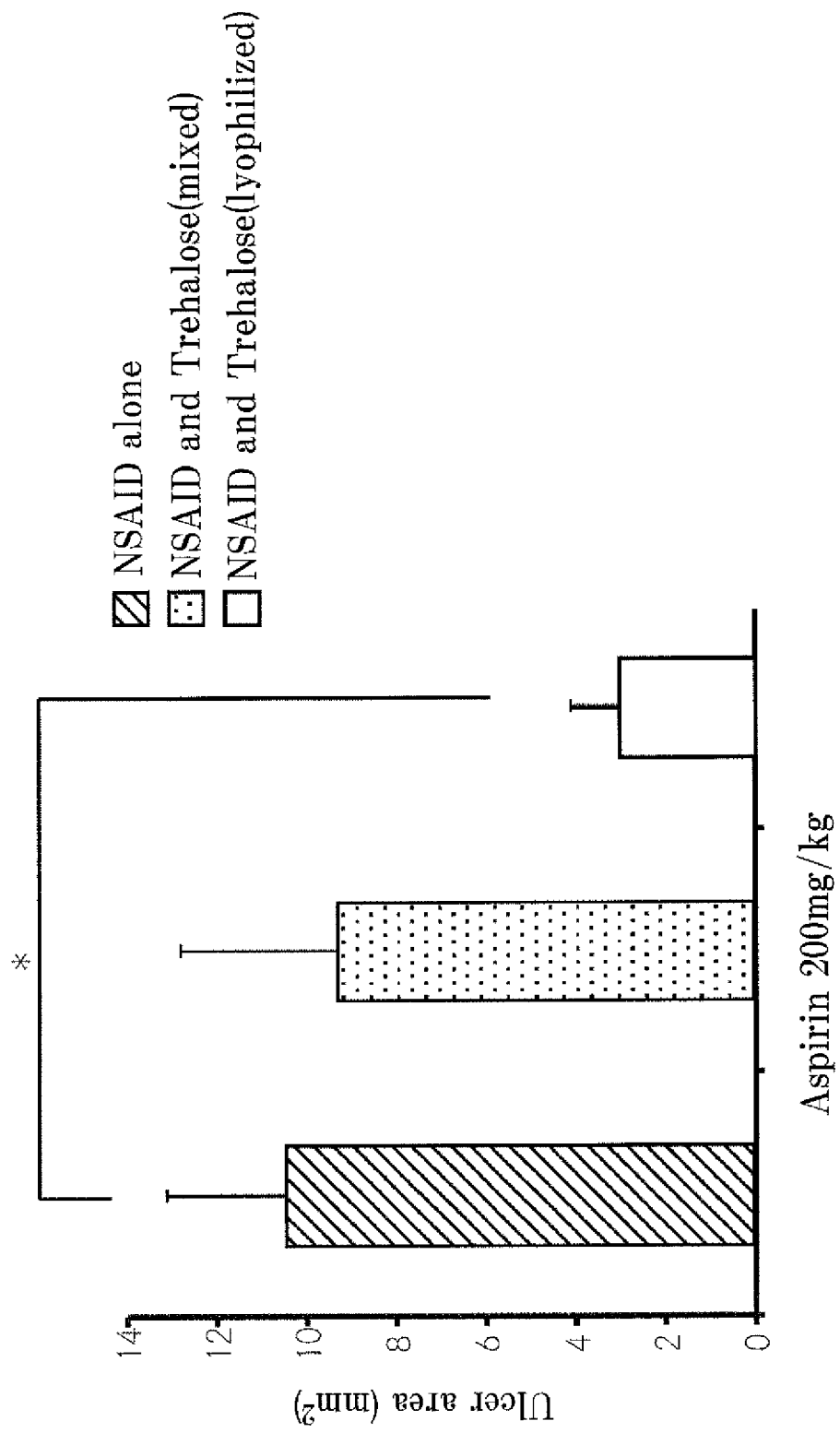
FIG. 3 shows a rat ulcer index ($mm^2$) when aspirin alone, a mixture of aspirin and trehalose and lyophilized aspirin and trehalose are administered.
Figure 4:
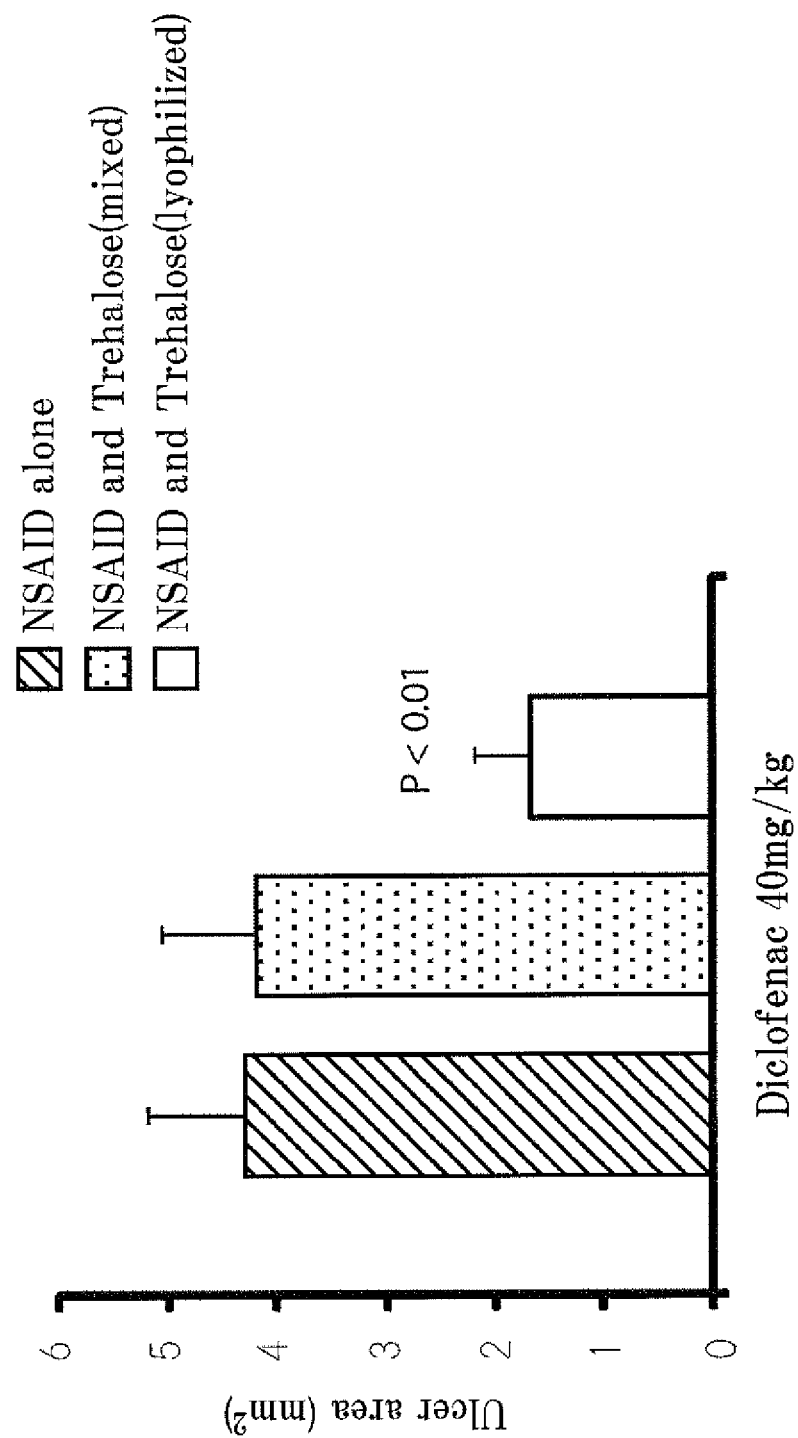
FIG. 4 shows a rat ulcer index ($mm^2$) when diclofenac alone, a mixture of diclofenac and trehalose and lyophilized diclofenac and trehalose are administered.

The results of ulcer index (mm²) when indomethacin, aspirin, or diclofenac was administered are shown in FIG. 2, FIG. 3, and FIG. 4.

FIG. 2 shows a rat ulcer index (mm²) when indomethacin alone, a mixture of indomethacin and trehalose and lyophilized indomethacin and trehalose are administered. The horizontal axis of the FIG. 2 indicates tested substances. The vertical axis of the FIG. 2 indicates ulcer area.

When indomethacin alone (30 mg/kg) was administered ulcer of 4.83±0.90 (average of 10 cases±standard deviation) mm² was observed. When mixture of indomethacin and trehalose (30 mg/kg of indomethacin and 800 mg/kg of trehalose) was administered ulcer of 4.15±0.86 (average of 5 cases±standard deviation) mm² was observed. Thus the rate of suppressed ulcer caused by mixed with trehalose was 14.0%. When lyophilized indomethacin and trehalose (30 mg/kg of indomethacin and 800 mg/kg of trehalose) was administered ulcer of 2.98±0.54 (average of 10 cases±standard deviation) mm² was observed. Thus the rate of suppressed ulcer caused by lyophilizing was 38.8%.

FIG. 3 shows a rat ulcer index (mm²) when aspirin alone, a mixture of aspirin and trehalose and lyophilized aspirin and trehalose are administered. The horizontal axis of the FIG. 3 indicates tested substances. The vertical axis of the FIG. 3 indicates ulcer area. In FIG. 3, the mark * indicates that there is effective difference.

When aspirin alone (200 mg/kg) was administered ulcer of 10.40±2.73 (average of 5 cases±standard deviation) mm² was observed. When mixture of aspirin and trehalose (200 mg/kg of aspirin and 800 mg/kg of trehalose) was administered ulcer of 9.25±3.54 (average of 5 cases±standard deviation) mm² was observed. Thus the rate of suppressed ulcer caused by mixed with trehalose was 11.5%. When lyophilized aspirin and trehalose (200 mg/kg of aspirin and 800 mg/kg of trehalose) was administered ulcer of 2.95±1.14 (average of 10 cases±standard deviation) mm² was observed. Thus the rate of suppressed ulcer caused by lyophilizing was 71.6%.

FIG. 4 shows a rat ulcer index (mm²) when diclofenac alone, a mixture of diclofenac and trehalose and lyophilized diclofenac and trehalose are administered. The horizontal axis of the FIG. 4 indicates tested substances. The vertical axis of the FIG. 4 indicates ulcer area. In the FIG. 4, p indicates a rejection rate. When diclofenac alone (40 mg/kg) was administered ulcer of 4.30±0.71 (average of 10 cases±standard deviation) mm² was observed. When mixture of diclofenac and trehalose (40 mg/kg of diclofenac and 800 mg/kg of trehalose) was administered ulcer of 4.20±1.11 (average of 5 cases±standard deviation) mm² was observed. Thus the rate of suppressed ulcer caused by mixed with trehalose was 2.3%. When lyophilized diclofenac and trehalose (40 mg/kg of diclofenac and 800 mg/kg of trehalose) was administered ulcer of 1.65±0.43 (average of 10 cases standard deviation) mm² was observed. Thus the rate of suppressed ulcer caused by lyophilizing was 61.6%.

The working example 2 shows that lyophilized NSAIDs and trehalose can effectively suppress ulcer.

Working Example 3

Suppression of Gastric mucosal disorder by molecular interactions between trehalose and NSAIDs 2

Cell viability and cell lethality were measured so as to investigate the suppression of gastric mucosa disorder caused by molecular interactions between NSAIDs (diclofenac) and trehalose. Powdered diclofenac alone (in FIGS. 5A and 5B, which is described as "Die") and lyophilized diclofenac and trehalose (weight rate diclofenac:trehalose=1:20; in FIGS. 5A and 5B, which is described as "Lyo") were added and were dissolved separately to DMEM media (Sigma) so that the final concentrate in the both of media became 2 mM. Then the media were added to 9 to 22 cells of oral epithelial cells Ca. The medium that comprised 1 mM diclofenac or the medium that comprised 1 mM diclofenac and 5% trehalose (diclofenac solution and trehalose solution were added separately to the medium; in FIGS. 5A and 5B, which is described as "Mix") were added to the 9 to 22 cells of Ca, which are different from those described above. All of the cells were incubated for 16 hours and cell viability and cell lethality were measured by means of LIVE/DEAD Assay (Molecular Probes). We also analyzed for the cells incubated by the usual medium as a control. In the example, the number of samples, N, were 4 to 6. The result is shown in FIGS. 5A and 5B.

Figure 5A:
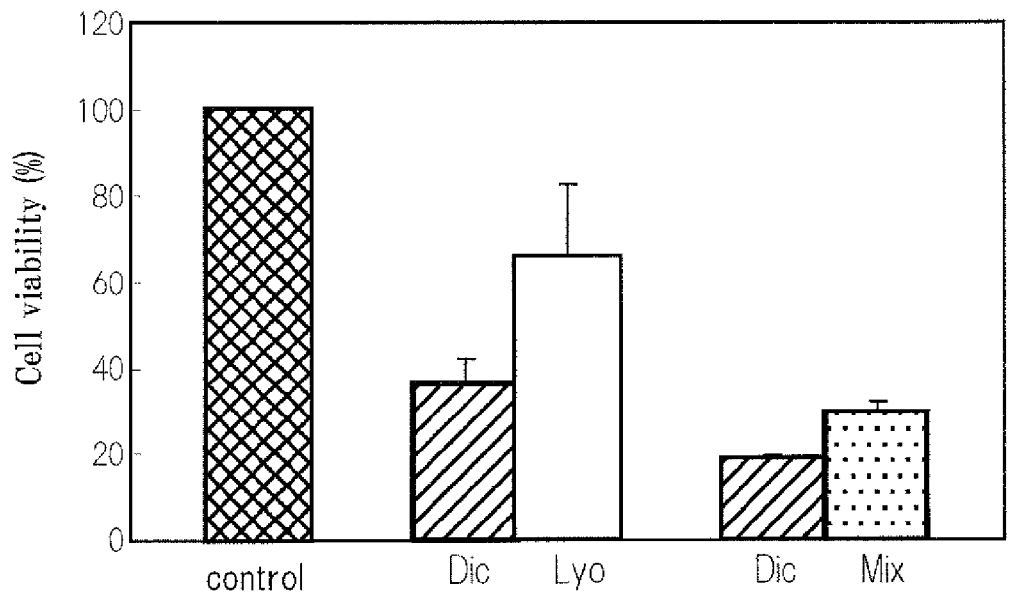
FIG. 5A shows an effect for gastric mucosal damages with lyophilized state and mixed state on cell viability rate.

FIG. 5A shows an effect for gastric mucosal damages with lyophilized state and mixed state on cell viability rate. The vertical axis of the FIG. 5A indicates cell viability [%] and higher value means more cells are alive. FIG. 5B shows cell lethality rate. The vertical axis of the FIG. 5B indicates cell lethality [%] and higher value means more cells have been dead. Thus high cell viability and low cell lethality indicate that cell disorder induced by diclofenac is suppressed.

Figure 5B:
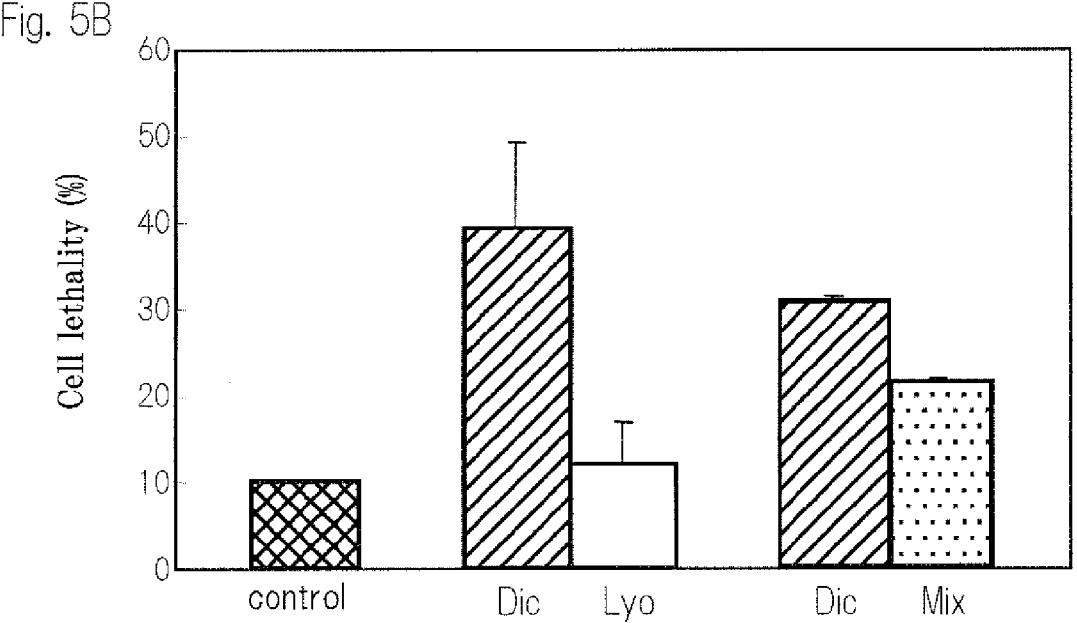
FIG. 5B shows cell lethality rate.

FIGS. 5A and 5B show that the mixed sample that was merely mixed with solutions ("Mix" in FIGS. 5A and 5B) had the effect of trehalose to suppress cell disorder induced by the diclofenac. However, lyophilized sample ("Lyo" in FIGS. 5A and 5B) shows more effect of suppressing cell disorder induced by the diclofenac.

Working Example 4

Investigate of intermolecular bonding between trehalose and NSAIDs

DSC, Differential Scanning calorimetry, was executed to investigate the intermolecular bonding between trehalose and NSAIDs (indomethacin, ibuprofen, aspirin, diclofenac, piroxicam, and Mefenamic acidic). DSC measurement was executed for trehalose alone, NSAIDs alone, mixture of trehalose and NSAIDs, and lyophilized trehalose and NSAIDs. The weight rate between trehalose and NSAIDs is shown in the following Table 5.

TABLE 5

| NSAIDs:Trehalose | Weight ratio |
|---|---|
| Indomethacin:Trehalose = | 3:80 |
| Ibuprofen:Trehalose = | 1:2 |
| Aspirin:Trehalose = | 1:4 |
| Diclofenac:Trehalose = | 1:20 |
| Piroxicam:Trehalose = | 3:80 |
| Mefenamic acid:Trehalose = | 1:4 |

Figure 6:
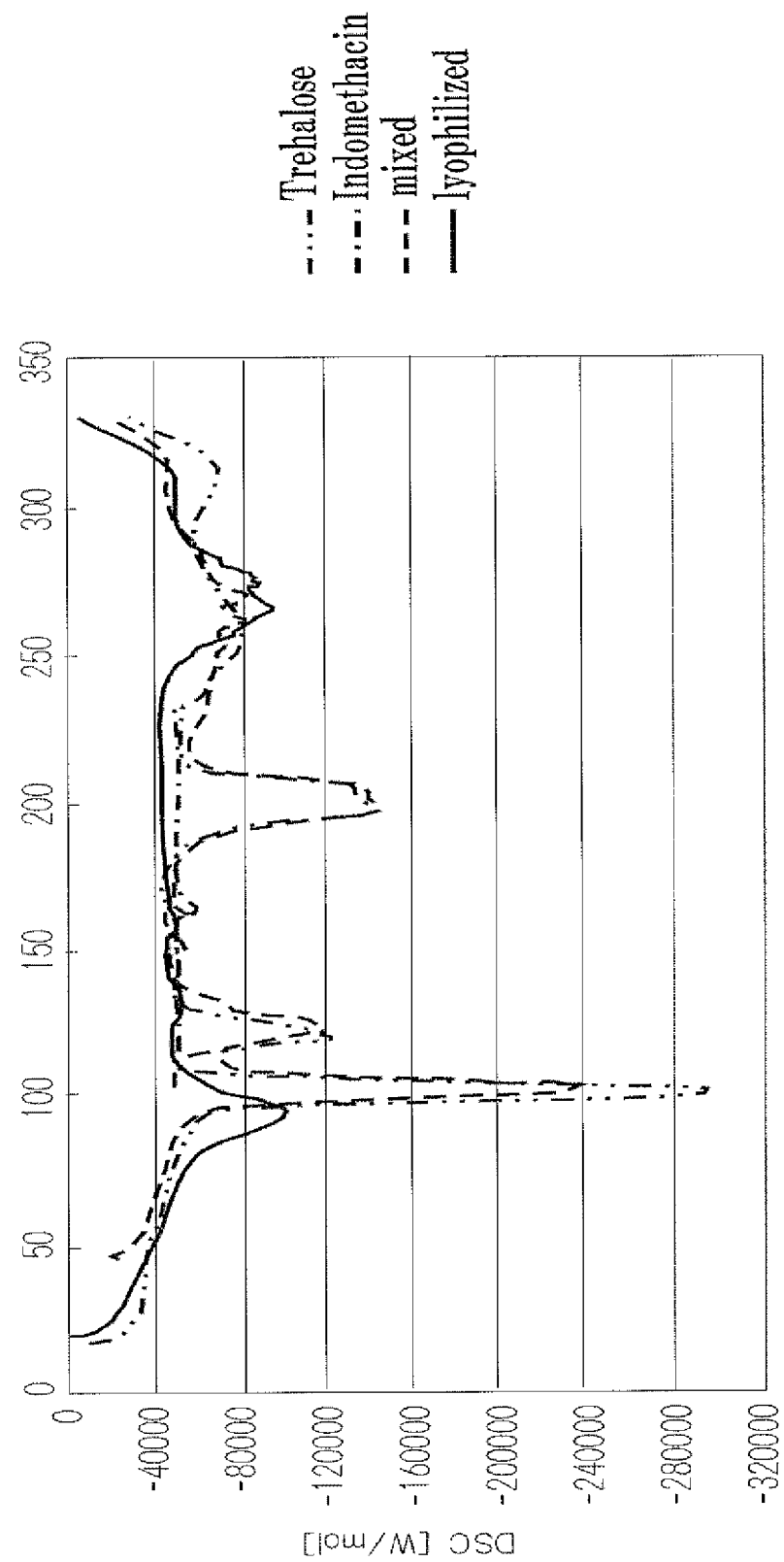
FIG. 6 shows the result of DSC of trehalose alone, indomethacin alone, a mixture of indomethacin and trehalose and lyophilized indomethacin and trehalose.
Figure 7:
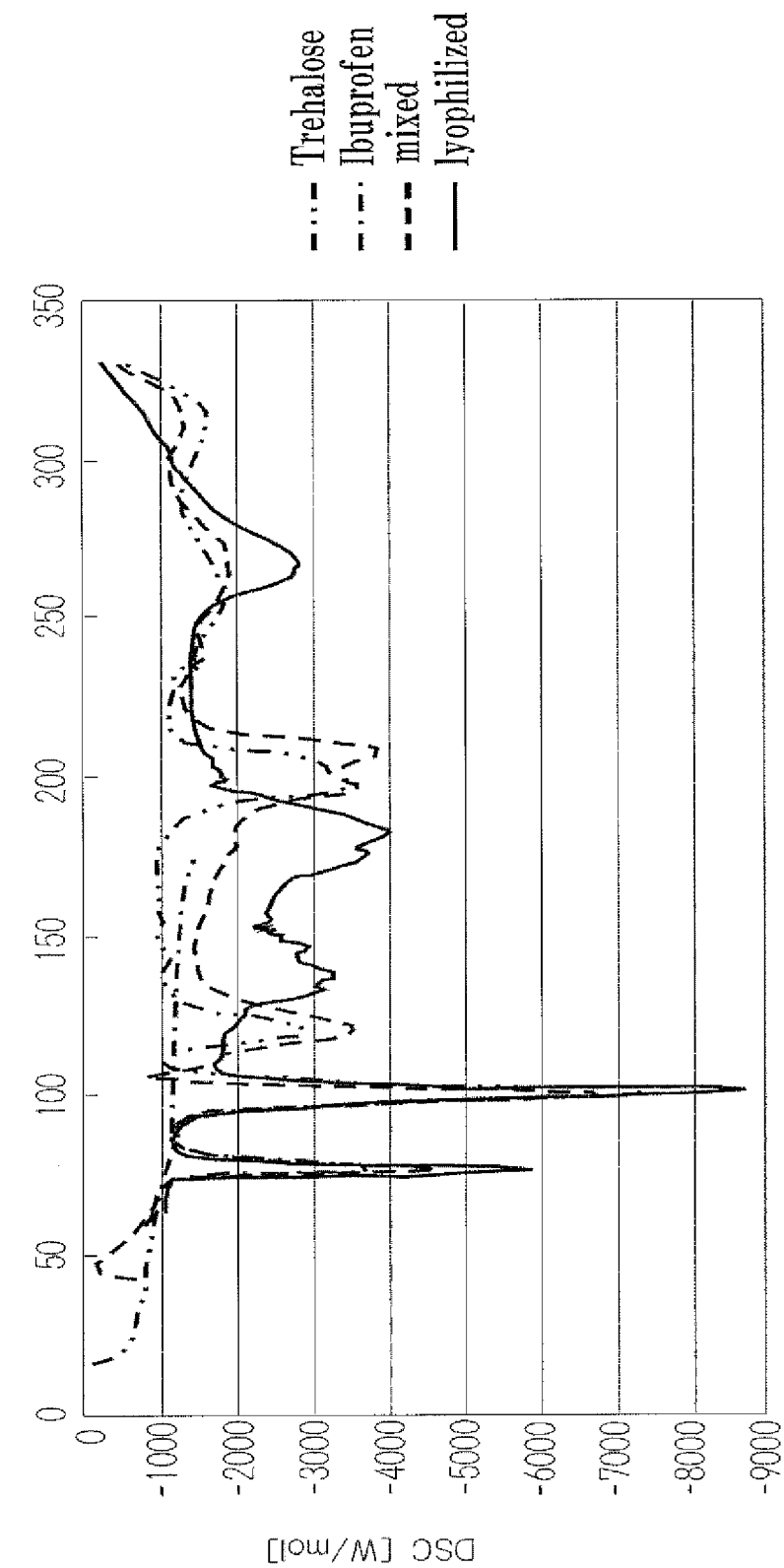
FIG. 7 shows the result of DSC of trehalose alone, ibuprofen alone, a mixture of ibuprofen and trehalose and lyophilized ibuprofen and trehalose.
Figure 8:
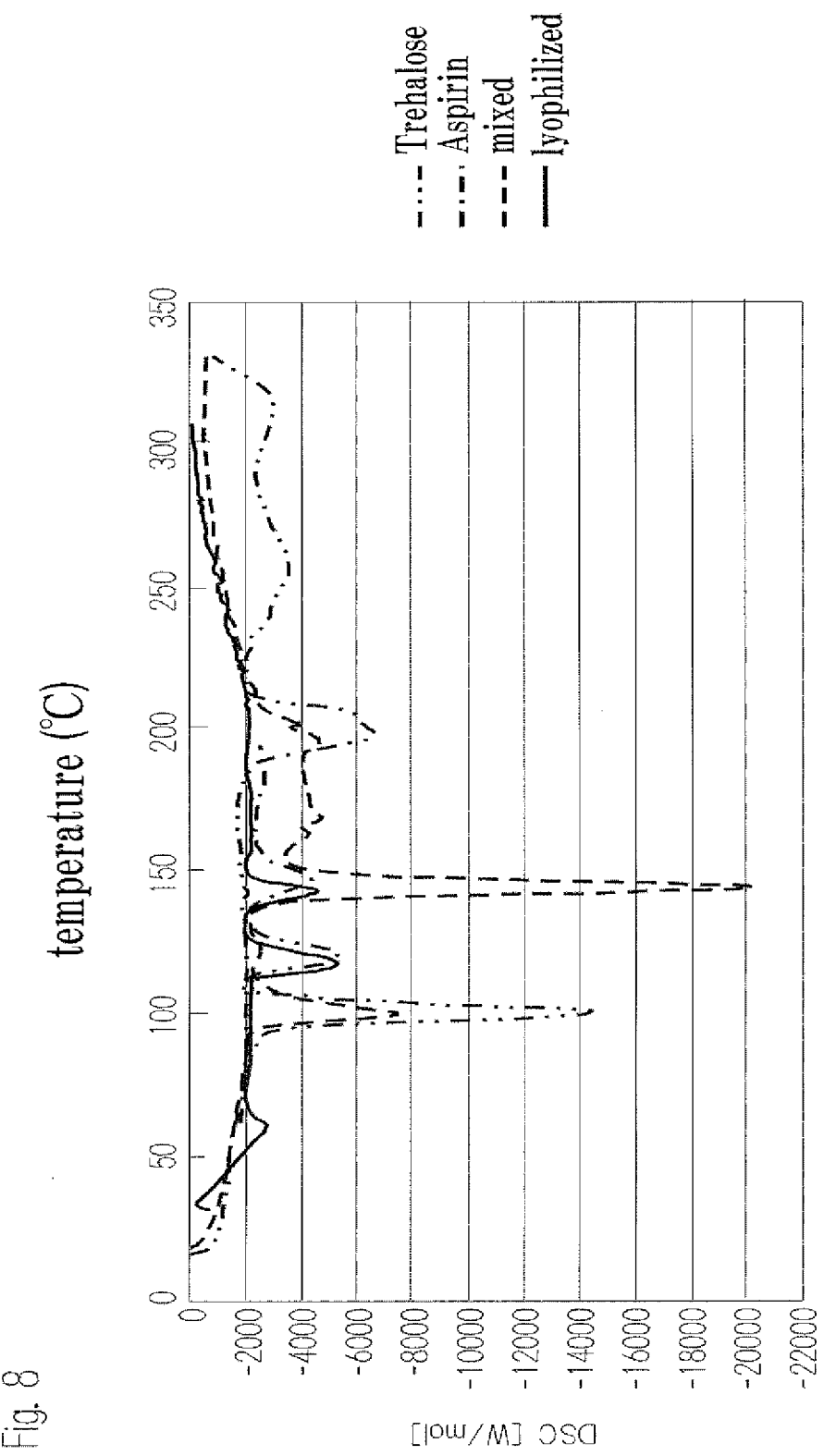
FIG. 8 shows the result of DSC of trehalose alone, aspirin alone, a mixture of aspirin and trehalose and lyophilized aspirin and trehalose.
Figure 9:
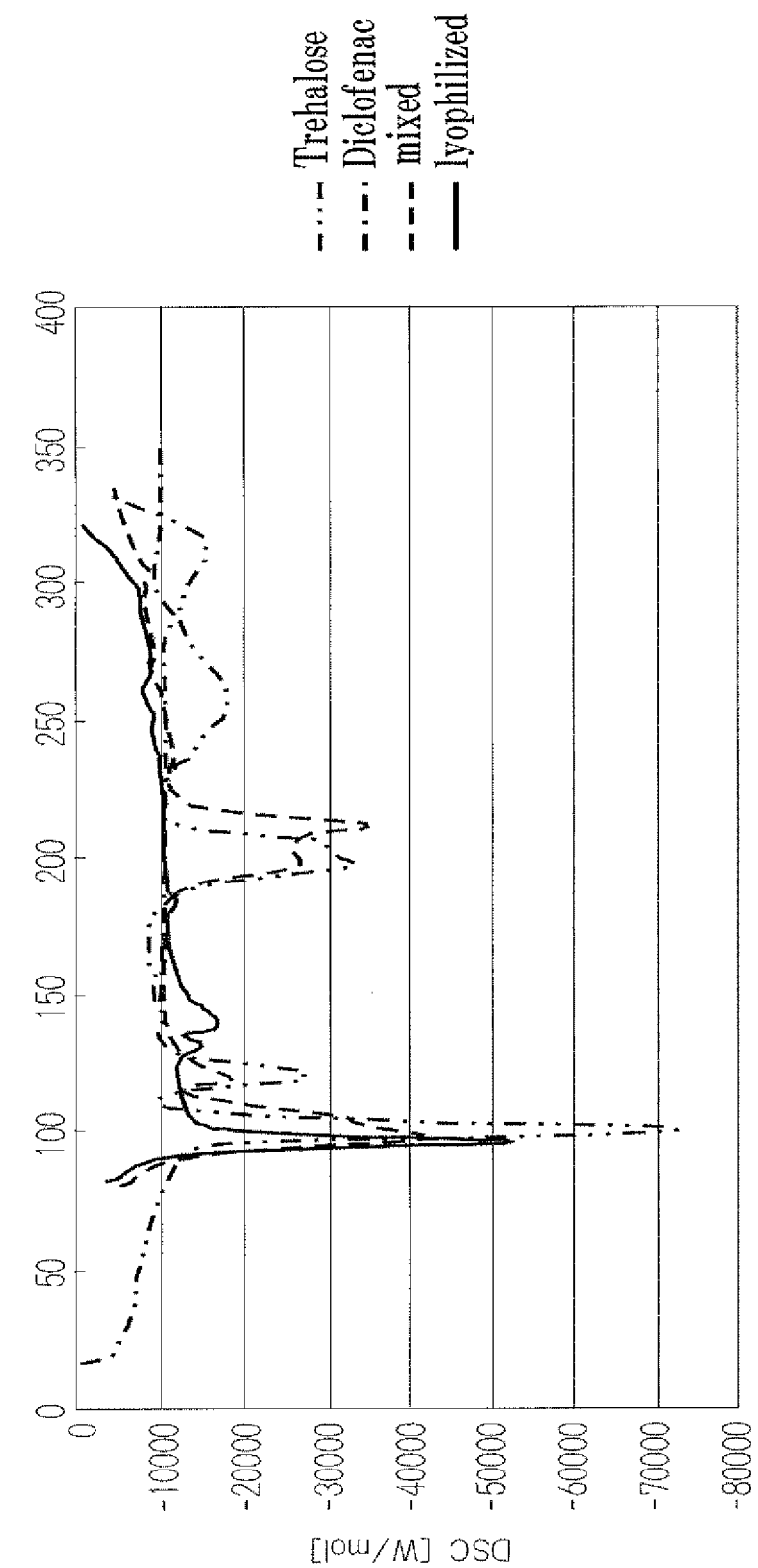
FIG. 9 shows the result of DSC of trehalose alone, diclofenac alone, a mixture of diclofenac and trehalose and lyophilized diclofenac and trehalose.
Figure 10:
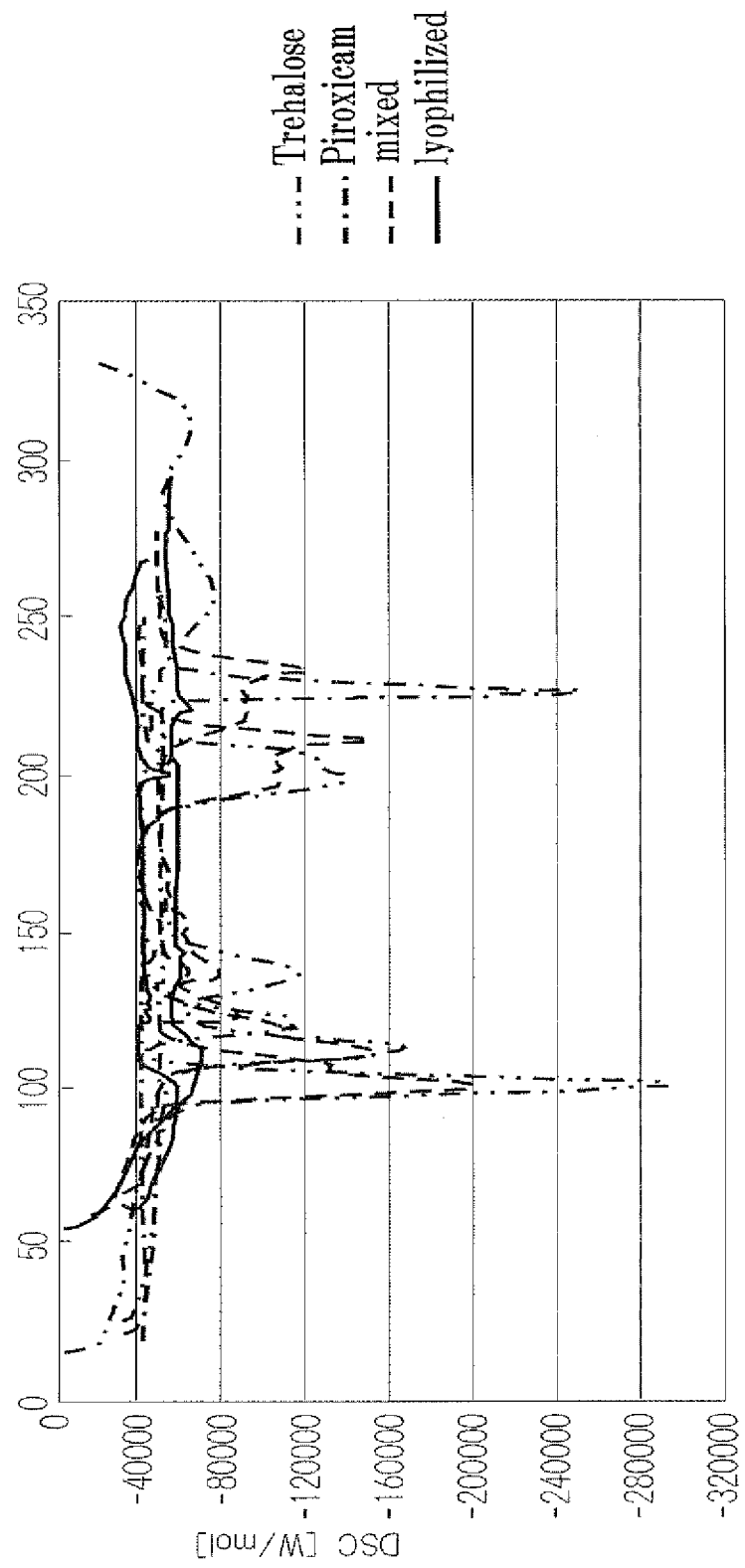
FIG. 10 shows the result of DSC of trehalose alone, piroxicam alone, a mixture of piroxicam and trehalose and lyophilized piroxicam and trehalose.
Figure 11:
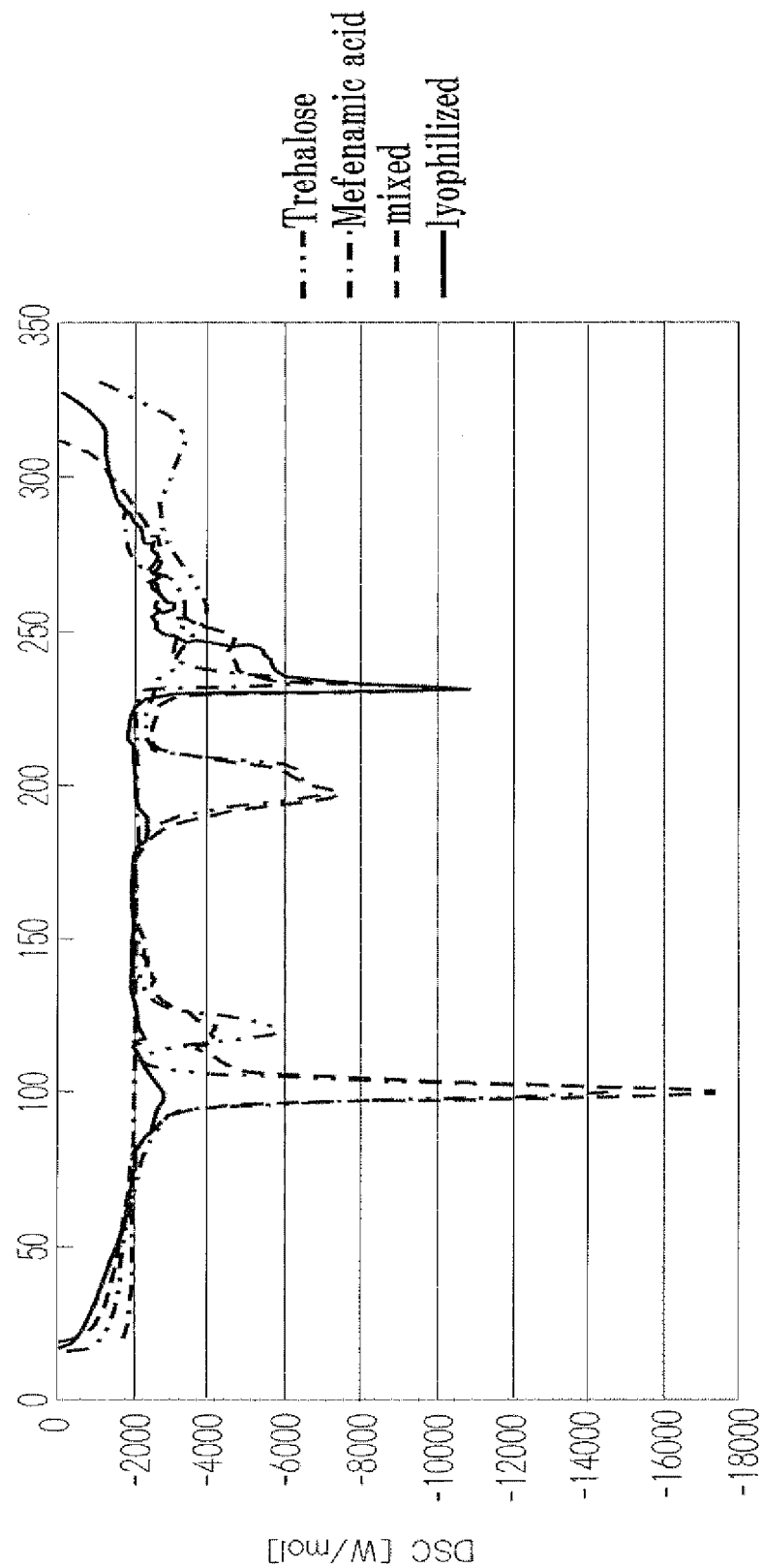
FIG. 11 shows the result of DSC of trehalose alone, Mefenamic acidic alone, a mixture of Mefenamic acidic and trehalose and lyophilized Mefenamic acidic and trehalose.

FIGS. 6 to 11 indicates the result of DSC measurement. FIG. 6 shows the result of DSC of trehalose alone, indomethacin alone, a mixture of indomethacin and trehalose and lyophilized indomethacin. FIG. 7 shows the result of DSC of trehalose alone, ibuprofen alone, a mixture of ibuprofen and trehalose and lyophilized ibuprofen. FIG. 8 shows the result of DSC of trehalose alone, aspirin alone, a mixture of aspirin and trehalose and lyophilized aspirin. FIG. 9 shows the result of DSC of trehalose alone, diclofenac alone, a mixture of diclofenac and trehalose and lyophilized diclofenac. FIG. 10 shows the result of DSC of trehalose alone, piroxicam alone, a mixture of piroxicam and trehalose and lyophilized piroxicam. FIG. 11 shows the result of DSC of trehalose alone, Mefenamic acidic alone, a mixture of Mefenamic acidic and trehalose and lyophilized Mefenamic acidic. In the FIGS. 6 to 11, the term "Mixture" means DSC curve for the mixture of trehalose and NSAIDs. In the FIGS. 6 to 11, the term "lyophilize" means DSC curve for the lyophilized trehalose and NSAIDs. In the FIGS. 6 to 11, the vertical axis indicates heat flow per mole [W/mol] for trehalose alone or NSAIDs alone. For the mixture and lyophilized compound, the vertical axis indicates heat flow per one mole of trehalose [W/mol] for the mixture and the lyophilized compound. In the FIGS. 6 to 11, the horizontal axis indicates temperature (° C.).

As shown in FIGS. 6 to 11, the peaks of the mixture of NSAIDs and trehalose are similar to the sum of the peaks of NSAIDs alone and the peaks of trehalose alone. To the contrary, in the DSC curve of lyophilized compound, the peak which is around 120° C. and derives from trehalose is extinguished or is shifted to low temperature direction or high temperature direction. These facts indicate that lyophilized compound has NSAIDs and trehalose that have interactive force between them.

The result shown in FIG. 6 indicates that the mixture of indomethacin and trehalose had the first peak at the region of 98 to 102° C., the second peak at the region of 190 to 210° C. and the third peak at the region of 115 to 125° C. The first peak means the highest peak (the largest peak of absolute value of DSC measured value) in a DSC curve.

The result of the mixture almost coincides with the peaks of DSC curve of trehalose alone.

The DSC curve of the lyophilized indomethacin and trehalose had the first peak at the region of 80 to 95° C. and the second peak at the region of 260 to 270° C. The DSC curve of the lyophilized indomethacin and trehalose further bad the third peak at the range of 270 to 280° C.

The differences of the positions of peaks between the mixture and the lyophilized compound indicate that the intermolecular compound of indomethacin and trehalose was generated by lyophilizing the mixed solution after indomethacin and trehalose were dissolved jointly.

The result shown in FIG. 7 indicates that the mixture of ibuprofen and trehalose had the first peak at the region of 98 to 102° C., the second peak at the region of 70 to 80° C., the third peak at the region of 190 to 210° C. and the fourth peak at the region of 115 to 125° C. The result of the mixture almost coincides with the peaks of DSC curves of trehalose alone and ibuprofen alone.

The DSC curve of the lyophilized ibuprofen and trehalose had the first peak at the region of 98 to 102° C. and the second peak at the region of 70 to 80° C., the third peak at the range of 175 to 190° C. and the fourth peak at the region of 130 to 145° C. Within the DSC peaks of lyophilized ibuprofen and trehalose, the peaks of at the range of 175 to 190° C. and at the region of 130 to 145° C. were not found in the DSC curve of the mixture. Thus it shows that the intermolecular compound of ibuprofen and trehalose was generated by lyophilizing the mixed solution after ibuprofen and trehalose were dissolved jointly.

The result shown in FIG. 8 indicates that the mixture of aspirin and trehalose had the first peak at the region of 145 to 150° C. and the second peak at the region of 98 to 102° C. The DSC curve of the lyophilized aspirin and trehalose had the first peak at the region of 110 to 120° C. and the second peak at the region of 135 to 145° C.

The differences of the positions of peaks between the mixture and the lyophilized compound indicate that the intermolecular compound of aspirin and trehalose was generated by lyophilizing the mixed solution after aspirin and trehalose were dissolved jointly.

The result shown in FIG. 9 indicates that the mixture of sodium diclofenac and trehalose had the first peak at the region of 95 to 110° C. and the second peak at the region of 190 to 220° C. The DSC curve of the lyophilized sodium diclofenac and trehalose had the first peak at the region of 90 to 100° C. and the second peak at the region of 135 to 145° C. The differences of the positions of peaks between the mixture and the lyophilized compound indicate that the intermolecular compound of sodium diclofenac and trehalose was generated by lyophilizing the mixed solution after sodium diclofenac and trehalose were dissolved jointly.

The result shown in FIG. 10 indicates that the mixture of Mefenamic acidic and trehalose had the first peak at the region of 98 to 102° C., the second peak at the region of 225 to 235° C. and the third peak at the region of 190 to 210° C. The DSC curve of the lyophilized Mefenamic acidic and trehalose had the first peak at the region of 225 to 235° C. and the second peak at the region of 90 to 110° C. The absolute values of peak top of the first peak and the second peak of the lyophilized compound (Absolute value of DSC measured value) are larger than the peaks at the regions of 225 to 235 and 90 to 110° C. for Mefenamic acidic alone.

The differences of the positions of peaks between the mixture and the lyophilized compound and the difference of SDC result between Mefenamic acidic and trehalose indicate that the intermolecular compound of Mefenamic acidic and trehalose was generated by lyophilizing the mixed solution after Mefenamic acidic and trehalose were dissolved jointly.

The result shown in FIG. 11 indicates that the mixture of piroxicam and trehalose had the first peak at the region of 98 to 102° C., the second peak at the region of 225 to 235° C. and the third peak at the region of 190 to 210° C. The DSC curve of the lyophilized piroxicam and trehalose had the first peak at the region of 90 to 105° C. and the second peak at the region of 195 to 205° C. The absolute values of peak top of the first peak and the second peak of the lyophilized compound (Absolute value of DSC measured value) are larger than the peaks at the regions of 90 to 105° C. and 195 to 205° C. The differences of the positions of peaks between the mixture and the lyophilized compound and the difference of SDC result between piroxicam and trehalose indicate that the intermolecular compound of piroxicam and trehalose was generated by lyophilizing the mixed solution after piroxicam and trehalose were dissolved jointly.

As shown in FIGS. 6 to 11, the peaks of the mixture of NSAIDs and trehalose are similar to the sum of the peaks of NSAIDs alone and the peaks of trehalose alone. To the contrary, in the DSC curve of lyophilized compound, the peak which is around 120° C. and derives from trehalose is extinguished or is shifted to low temperature direction or high temperature direction. These facts indicate that lyophilized compound has NSAIDs and trehalose that have interactive force between them.

As described the above, the medical drugs that comprise trehalose and NSAIDs that have molecular interactions between them, thereby it can alleviate damage of gastrointestinal mucosal induced by NSAIDs, such as disorder of gastric mucosa induced by NSAIDs. Thus it is shown that the medical drugs of the invention reduce damage of gastrointestinal mucosal induced by NSAIDs.

Working Example 5

Figure 12:
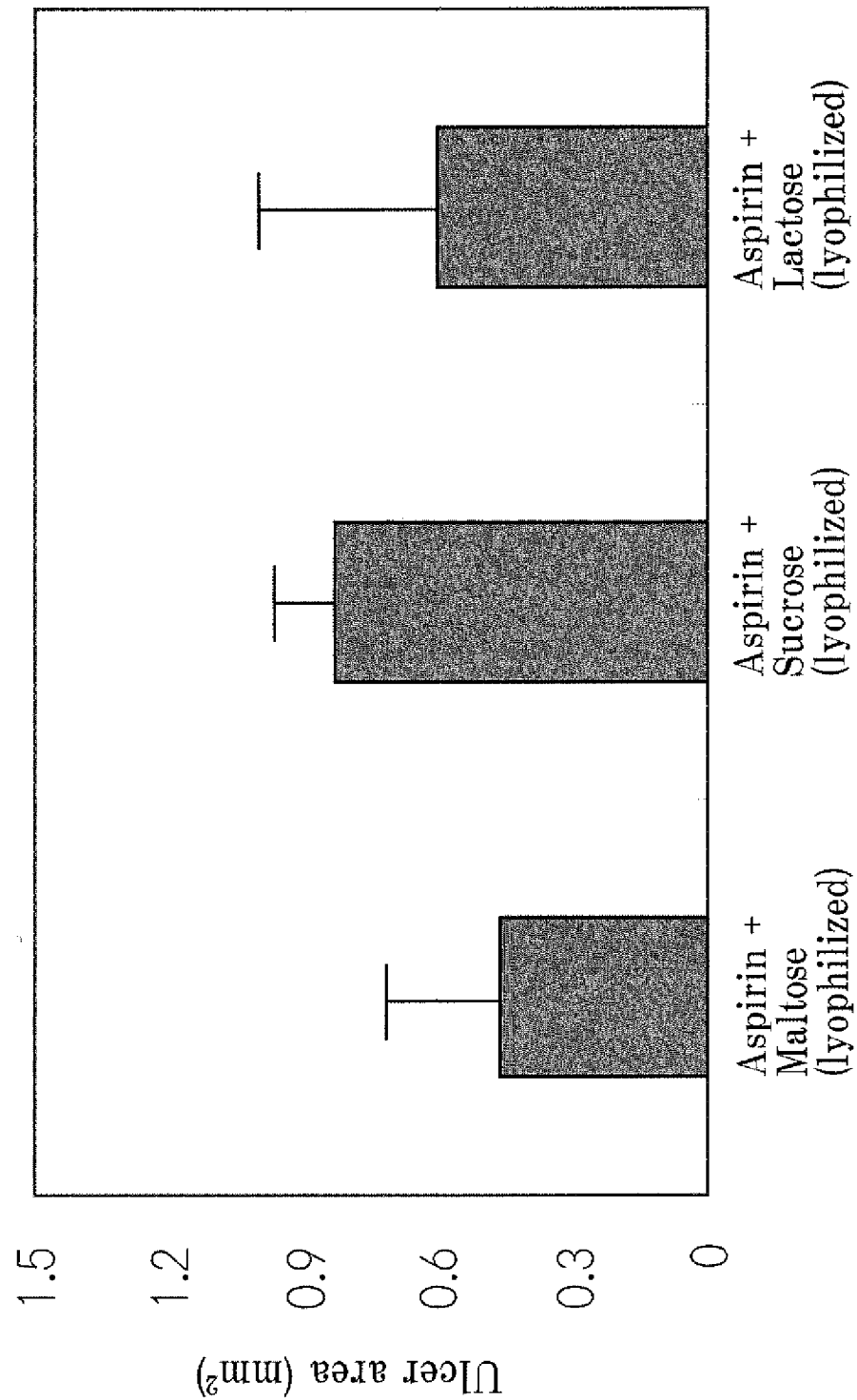
FIG. 12 shows the result of measurement of ulcer area when each of maltose, sucrose, and lactose were lyophilized with aspirin to conform a molecular compound.

Ulcer area was measured by the same conditions in working example 2 except for replacing trehalose with maltose, sucrose, or lactose. We fainted lyophilized molecular compound of aspirin with disaccharide (maltose, sucrose, or lactose). The obtained ulcer area is shown in FIG. 12. Compared to FIG. 3 and FIG. 12, it is shown that aspirin effectively suppress ulcer by forming molecular compound of aspirin with disaccharide.

Working Example 6

Figure 13:
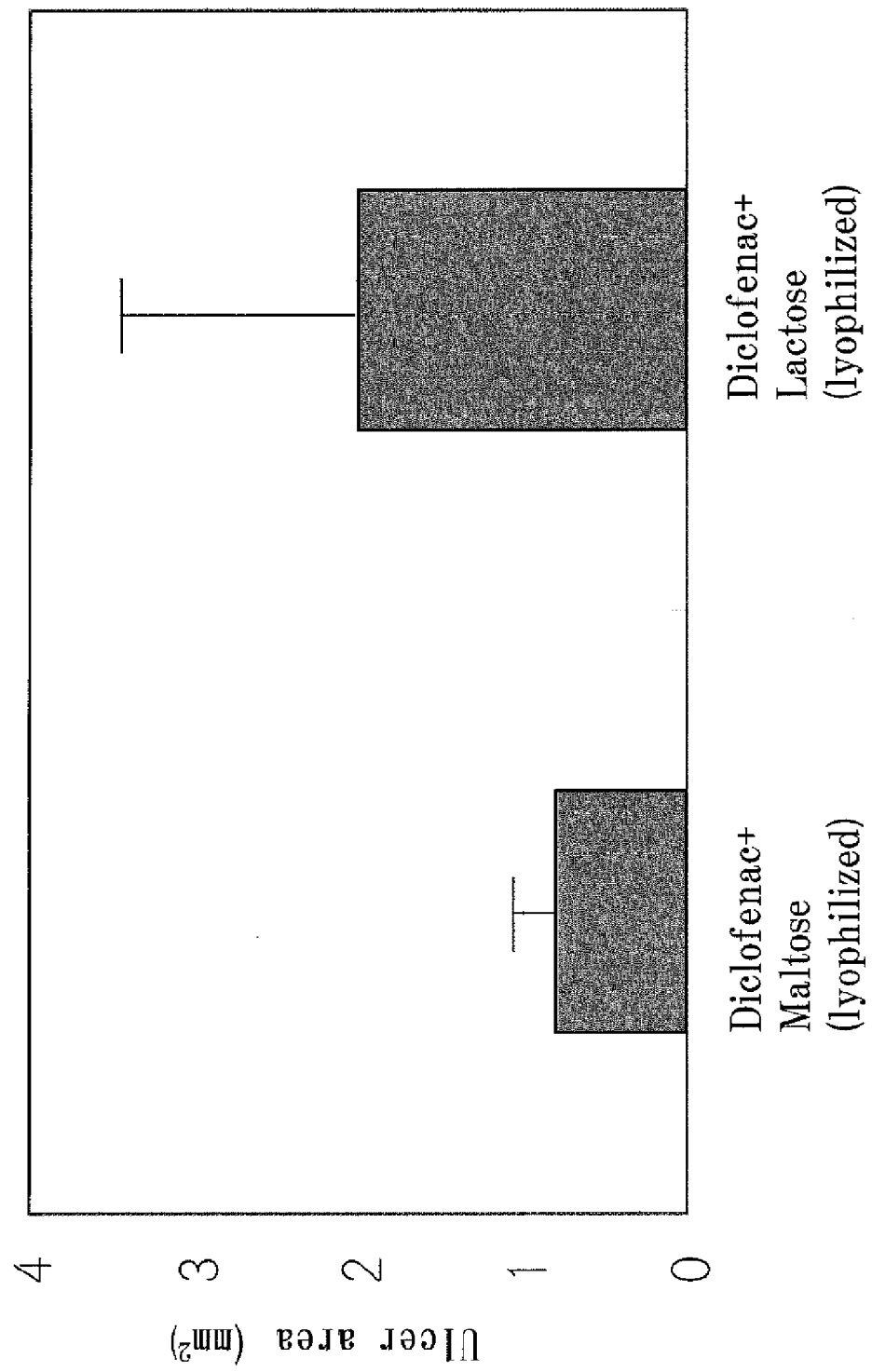
FIG. 13 shows the result of measurement of ulcer area when each of maltose and lactose were lyophilized with diclofenac to conform a molecular compound.

Ulcer area was measured by the same conditions in working example 2 except for replacing trehalose with maltose, or lactose. We formed lyophilized molecular compound of diclofenac with disaccharide (maltose, or lactose). The obtained ulcer area is shown in FIG. 13. Compared to FIG. 4 and FIG. 13, it is shown that diclofenac effectively suppress ulcer by forming molecular compound of diclofenac with disaccharide.

INDUSTRIAL APPLICABILITY

The present invention may be used in medical industry.

What is claimed is:

1. A method of manufacturing a medical drug comprising an intermolecular compound of trehalose and a non-steroidal anti-inflammatory drug, NSAID, the method comprising:
   dissolving the trehalose and the NSAID into one or more solutions to form an approximately homogenously-mixed liquid mixture of dissolved trehalose and dissolved NSAID, wherein the liquid mixture contains the intermolecular compound and a weight ratio of the trehalose to the NSAID in the liquid mixture is 1:1 to 30:1; and
   drying the liquid mixture so as to obtain the medical drug.

2. The method according to claim 1, wherein the NSAID is an acidic NSAID.

3. The method according to claim 1, wherein the NSAID is one or more selected from the group consisting of Aspirin, Sodium salicylate, Salicylamide, Sazapirin, Diflunisal, Ethenzamide, Aluminum aspirin, 5-Amino salicylic acidic, Indomethacin, Etodolac, Sodium diclofenac, Sulindac, Sodium Amfenac, Proglumetacin Maleate, Acemetacin, Nabumeton, Mofezolac, Ibuprofen, Naproxen, Loxoprofen, Flurbiprofen, Flurbiprofen Axetil, Oxaprozin, Tiaprofenic acidic, Pranoprofen, Aluminoprophen, Zaltoprofen, Mefenamic acidic, TolFenamic acidic, Alminum flufenamate, Ketophenylbutazone, Clofezone, Bucolome, Piroxicam, Lornoxicam, Tenoxicam, Meloxicam, Ampiroxicam, Epirizole, Tiaramide, and Emorfazone.

4. The method according to claim 1, wherein the weight ratio of the trehalose to the NSAID in the liquid mixture is 2:1 to 30:1.

5. The method according to claim 1, wherein the medical drug induces anti-inflammatory effect of the NSAID and alleviates gastrointestinal mucosal damage induced by the NSAID.

* * * * *